(12) United States Patent
Weitz et al.

(10) Patent No.: US 12,345,708 B2
(45) Date of Patent: Jul. 1, 2025

(54) MICROFLUIDIC DETERMINATION OF IMMUNE AND OTHER CELLS

(71) Applicant: President and Fellows of Harvard College, Cambridge, MA (US)

(72) Inventors: David A. Weitz, Cambridge, MA (US); Li Sun, Cambridge, MA (US); John Heyman, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1077 days.

(21) Appl. No.: 16/087,203

(22) PCT Filed: Mar. 24, 2017

(86) PCT No.: PCT/US2017/024058
§ 371 (c)(1),
(2) Date: Sep. 21, 2018

(87) PCT Pub. No.: WO2017/165791
PCT Pub. Date: Sep. 28, 2017

(65) Prior Publication Data
US 2019/0101537 A1    Apr. 4, 2019

Related U.S. Application Data

(60) Provisional application No. 62/313,339, filed on Mar. 25, 2016.

(51) Int. Cl.
| | | |
|---|---|---|
| G01N 33/569 | (2006.01) |
| B01L 3/00 | (2006.01) |
| C12N 5/0781 | (2010.01) |
| C12N 5/0783 | (2010.01) |
| C12Q 1/6895 | (2018.01) |
| G01N 33/573 | (2006.01) |
| G01N 33/68 | (2006.01) |

(52) U.S. Cl.
CPC .. *G01N 33/56972* (2013.01); *B01L 3/502792* (2013.01); *C12N 5/0635* (2013.01); *C12N 5/0636* (2013.01); *C12Q 1/6895* (2013.01); *G01N 33/573* (2013.01); *G01N 33/6863* (2013.01); *C12Q 2600/13* (2013.01)

(58) Field of Classification Search
None
See application file for complete search history.

(56) References Cited

U.S. PATENT DOCUMENTS

| | | | |
|---|---|---|---|
| 7,708,949 B2 | 5/2010 | Stone et al. | |
| 8,337,778 B2 | 12/2012 | Stone et al. | |
| 9,176,504 B2* | 11/2015 | Chiou | B01L 3/502715 |
| 10,473,647 B1* | 11/2019 | Anderson | G01N 33/6869 |
| 2002/0061847 A1* | 5/2002 | Wheeler | C07K 14/705 |
| | | | 514/19.6 |
| 2003/0207326 A1* | 11/2003 | Su | G01N 33/48721 |
| | | | 435/7.1 |
| 2004/0241759 A1 | 12/2004 | Tozer et al. | |
| 2006/0023559 A1 | 2/2006 | Xu et al. | |
| 2006/0163385 A1 | 7/2006 | Link et al. | |
| 2007/0003442 A1 | 1/2007 | Link et al. | |
| 2007/0065946 A1* | 3/2007 | Reboud | G01N 33/5008 |
| | | | 436/63 |
| 2008/0063634 A1* | 3/2008 | Salfeld | A61P 33/00 |
| | | | 530/402 |
| 2009/0068170 A1 | 3/2009 | Weitz et al. | |
| 2009/0131543 A1 | 5/2009 | Weitz et al. | |
| 2010/0068754 A1 | 3/2010 | Kirakossian | |
| 2010/0092955 A1 | 4/2010 | Harriman | |
| 2010/0120047 A1 | 5/2010 | Forsyth | |
| 2010/0172803 A1 | 7/2010 | Stone et al. | |
| 2011/0275063 A1 | 11/2011 | Weitz et al. | |

(Continued)

FOREIGN PATENT DOCUMENTS

| | | | |
|---|---|---|---|
| CN | 102388145 A | 3/2012 | |
| WO | WO 2004/002627 A2 | 1/2004 | |

(Continued)

OTHER PUBLICATIONS

Lagus et al., "High-throughput co-encapsulation of self-ordered cell trains: cell pair interactions in microdroplets", RSC Adv., 2013, 3, 20512-20522.*
Chinese Office Action for Application No. 201480053909.1 mailed Feb. 25, 2020.
Yuan et al., Droplet encapsulation improves accuracy of immune cell cytokine capture assays. Lab Chip. Apr. 21, 2020;20(8):1513-1520. doi: 10.1039/c91c01261c. Epub Apr. 3, 2020.
CN 201480053909.1, Feb. 25, 2020, Chinese Office Action.
U.S. Appl. No. 14/912,685, filed Feb. 18, 2016, Weitz et al.

(Continued)

*Primary Examiner* — Ann Montgomery
(74) *Attorney, Agent, or Firm* — Wolf, Greenfield & Sacks, P.C.

(57) ABSTRACT

The present invention generally relates to fluidic droplets and systems and methods for determining immune or other cells. Some aspects of the invention are generally directed to assays that combine sensitive detection of secreted products with detection of target cell death in droplets containing an effector cell, systems and methods to isolate droplets in which one or more cell interactions have occurred, or systems and methods to generate nucleic acid information from cell interactions. In addition, some embodiments of the invention are generally directed to containing two (or more) cells in droplets, e.g., an effector cell and one or more target cells, and determining various interactions between the cells within the droplets, such as whether the effector cell kills the target cell, whether the effector cell releases antibodies, cytokines or other substances that are able to interact with the target cell or are released in the presence of the target cell, or the like.

20 Claims, 5 Drawing Sheets

(56) References Cited

U.S. PATENT DOCUMENTS

| | | | |
|---|---|---|---|
| 2012/0004185 A1 | 1/2012 | Greene | |
| 2012/0122714 A1* | 5/2012 | Samuels | C12Q 1/6874 |
| | | | 506/18 |
| 2012/0149592 A1 | 6/2012 | Love et al. | |
| 2014/0128276 A1 | 5/2014 | Li et al. | |
| 2014/0338753 A1 | 11/2014 | Sperling et al. | |
| 2015/0190506 A1* | 7/2015 | Cheung | A61K 38/16 |
| | | | 424/134.1 |
| 2015/0346201 A1* | 12/2015 | Korny | G01N 21/6458 |
| | | | 506/13 |
| 2016/0201129 A1 | 7/2016 | Weitz et al. | |

FOREIGN PATENT DOCUMENTS

| | | | |
|---|---|---|---|
| WO | WO 2004/091763 A2 | | 10/2004 |
| WO | WO 2005/021151 A1 | | 3/2005 |
| WO | WO 2006/096571 A2 | | 9/2006 |
| WO | WO 2009/011808 A1 | | 1/2009 |
| WO | WO 2009/020633 A2 | | 2/2009 |
| WO | WO 2009026448 | * | 2/2009 ............ G01N 33/53 |
| WO | WO 2009/120254 A1 | | 10/2009 |
| WO | WO 2010/005593 A1 | | 1/2010 |
| WO | WO 2010/151776 A2 | | 12/2010 |
| WO | WO 2012/167142 A2 | | 12/2012 |
| WO | WO 2013/095737 A2 | | 6/2013 |
| WO | WO 2013/126774 A2 | | 8/2013 |
| WO | WO 2015/031190 A1 | | 3/2015 |
| WO | WO 2017/165791 A1 | | 9/2017 |

OTHER PUBLICATIONS

Cn 201480053909.1, Jul. 4, 2018, Chinese Office Action.
EP 14840425.4, Apr. 24, 2017, Extended European Search Report.
PCT/US2014/052271, Dec. 4, 2014, International Search Report and Written Opinion.
PCT/US2014/052271, Mar. 10, 2016, International Preliminary Report on Patentability.
PCT/US2017/024058, Jun. 16, 2017, International Search Report and Written Opinion.
PCT/US2017/024058, Oct. 4, 2018, International Preliminary Report on Patentability.
Chinese Office Action for mailed Jul. 4, 2018 for Application No. 201480053909.1.
Extended European Search Report mailed Apr. 24, 2017 for Application No. EP 14840425.4.
International Search Report and Written Opinion mailed Dec. 4, 2014 for Application No. PCT/US2014/052271.
International Preliminary Report on Patentability mailed Mar. 10, 2016 for Application No. PCT/US2014/052271.
International Search Report and Written Opinion mailed Jun. 16, 2017 for Application No. PCT/US2017/024058.
International Preliminary Report on Patentability mailed Oct. 4, 2018 for Application No. PCT/US2017/024058.
Office Action mailed Jan. 16, 2018 for U.S. Appl. No. 16/087,203.
Final Office Action mailed Jun. 11, 2018 for U.S. Appl. No. 16/087,203.
Brouzes et al., Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Konry et al., Droplet-based microfluidic platforms for single T cell secretion analysis of IL-10 cytokine. Biosens Bioelectron. Jan. 15, 2011;26(5):2707-10. doi: 10.1016/j.bios.2010.09.006. Epub Sep. 15, 2010.
Konry et al., Ultrasensitive Detection of Low-Abundance Surface-Marker Protein using Isothermal Rolling Circle Amplification in Microfluidic Nano-Liter Platform. Small. Jun. 27, 2012:1-10. Author manuscript.
Serganova et al., Metabolic imaging: a link between lactate dehydrogenase A, lactate, and tumor phenotype. Clin Cancer Res. Oct. 1, 2011;17(19):6250-61. doi: 10.1158/1078-0432.CCR-11-0397. Epub Aug. 15, 2011.
Tumarkin et al., High-throughput combinatorial cell co-culture using microfluidics. Integr Biol (Camb). Jun. 2011;3(6):653-62. doi: 10.1039/c1ib00002k. Epub Apr. 28, 2011.

* cited by examiner

MICROFLUIDIC DETERMINATION OF IMMUNE AND OTHER CELLS

RELATED APPLICATIONS

This application is a national stage filing under 35 U.S.C. § 371 of International Patent Application Serial No. PCT/US2017/024058, filed Mar. 24, 2017, entitled "Microfluidic Determination of Immune and Other Cells," which claims the benefit of U.S. Provisional Patent Application Ser. No. 62/313,339, filed Mar. 25, 2016, entitled "Microfluidic Determination of Immune Cells," by Weitz, et al., each of which is incorporated herein by reference in its entirety.

GOVERNMENT FUNDING

This invention was made with government support under EB014703 and GM113420awarded by National Institutes of Health (NIH) and under 1310266 and 1420570 awarded by National Science Foundation (NSF) and under HR0011-11-C-0093 awarded by U.S. Department of Defense/Defense Advanced Research Projects Agency (DOD/DARPA). The government has certain rights in this invention.

FIELD

The present invention generally relates to fluidic droplets and systems and methods for determining immune or other cells.

BACKGROUND

An integral part of the human adaptive immune response is the specific recognition of foreign/misfolded proteins (antigens) by lymphocytes through their highly specialized protein receptors on the cell surface. These receptors are generated by a remarkable DNA rearrangement mechanism during lymphocyte development that produces millions of the variants of the receptor encoding genes. Each cell has only one set of fully rearranged genes and produces many receptor proteins of the same sequence. Thus, an immune system's ability to recognize an enormous diversity of antigens results from the generation of a large number of immune cells, each of which presents a unique species of receptor. If a person develops a tumor or is infected by a virus such as HIV, lymphocytes with receptors that can recognize proteins derived from these entities will take action to eradicate the tumor cells or the HIV infected host cells. These lymphocytes may also be termed effector cells. Theoretically, due to the diversity of the receptors, an individual's immune cell population should contain effector cells that recognize antigens derived from virtually any type of disease.

However, the survival rate of cancer and AIDS patients can be very low. This is because antigen-specific effector cells are often so scarce that they are unable to prevent disease progression, which is especially true for some malignant tumors and for viruses that propagate rapidly.

One way to solve this problem is to first harvest disease-specific effector cells, then grow them to a large population in vitro and finally infuse them back into the subject. Alternatively, effector T cells with desired activity can be isolated and the DNA encoding their T cell receptors can be identified and used to create a population of effector cells with desired specificity to target cells. These genetically modified cells can be cultured to high numbers and infused into the subject. These two examples are types of adoptive cell therapy.

Presently, adoptive cell therapy is mainly used to treat cancer, especially melanoma and leukemia Cell selection and growth is currently performed through a process called limiting dilution where a subject's tumor cells (or antigens derived from tumor cells) and lymphocytes are grown together in well plates (called "stimulation") in successive dilutions. Those wells with lymphocytes that respond to this stimulation through cytokine secretion which is tested afterward through an ELISA assay for each well are selected. The cells from the selected wells are then expanded to reach a desired population of effector cells.

However, the limiting dilution method to select and grow clones of effector cells has limitations. It is performed in microwell plates, and cytokine secretion from a single cell cannot be detected in the relatively large 2 microliter minimum working volume. A well-based cytokine secretion assay requires hundreds of cells per well. In addition, because there are usually several antigens associated with a single disease, it is not possible to associate a single effector cell with its specific target antigen using these assays. Therefore, this process cannot effectively select individual effector cells that detect specific disease-related antigens and cannot be used to identify specific T-cell receptors.

The limiting dilution method is also relatively low throughput. In most disease states, useful effector cells will be rare, at a frequency of $1/1000$ or $1/10,000$ total CD8+ T-cells. Thus, a well-plate assay is insufficient to generate a functional population of effector cells without many generations of cell expansion. This is important in adoptive cell therapy (which requires billions of cells), as it is desirable to minimize a subject's wait-time and previous research has shown that effector cells become less active with an increased number of cell-division cycles.

Accordingly, improvements in effector cell identification are needed.

SUMMARY

The present invention generally relates to fluidic droplets and systems and methods for determining immune or other cells. The subject matter of the present invention involves, in some cases, interrelated products, alternative solutions to a particular problem, and/or a plurality of different uses of one or more systems and/or articles.

In one aspect, the present invention is generally directed to a method comprising containing, in a microfluidic droplet, an immune cell, a target cell, a first signaling entity that determines cell viability, and a second signaling entity that determines a cytokine; determining the first signaling entity within the droplet to determine viability of the immune cell and/or the target cell; and determining the second signaling entity within the droplet to determine the cytokine within the droplet. In some cases, the second signaling entity is distinguishable from the first signaling entity.

The method, in another aspect, is generally directed to a method including encapsulating, in a microfluidic droplet, an immune cell, a target cell, a first signaling entity that determines cell viability, and a second signaling entity that determines a cytokine, wherein the first signaling entity comprises a first fluorescent entity, and wherein the second signaling entity is distinguishable from the first signaling entity; determining the first signaling entity within the droplet to determine viability of the immune cell and/or the target cell; and determining the second signaling entity within the droplet to determine the cytokine within the droplet.

In yet another aspect, the method includes acts of containing an immune cell and a target cell in a droplet, determining whether the target cell in the droplet is alive or dead, and determining a cytokine within the droplet released by the immune cell.

In another aspect, the present invention encompasses methods of making one or more of the embodiments described herein, for example, determining immune or other cells. In still another aspect, the present invention encompasses methods of using one or more of the embodiments described herein, for example, determining immune or other cells.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
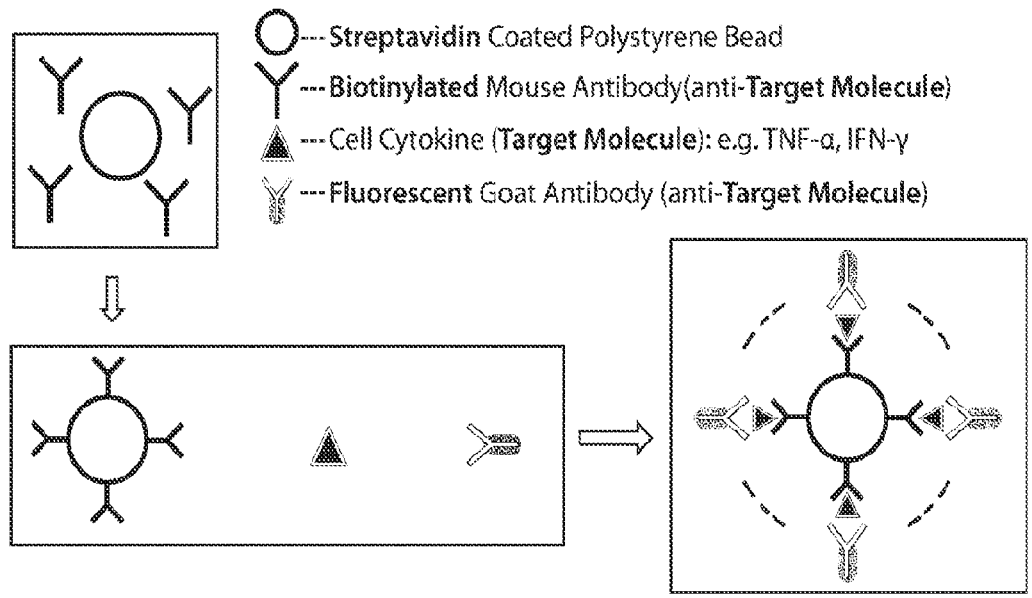
FIG. 1 illustrates a cytokine detection technique in accordance with certain embodiments of the invention.

The present invention generally relates to fluidic droplets and systems and methods for determining immune or other cells. Some aspects of the invention are generally directed to assays that combine sensitive detection of secreted products with detection of target cell death in droplets containing an effector cell, systems and methods to isolate droplets in which one or more cell interactions have occurred, or systems and methods to generate nucleic acid information from cell interactions. In addition, some embodiments of the invention are generally directed to containing two (or more) cells in droplets, e.g., an effector cell and one or more target cells, and determining various interactions between the cells within the droplets, such as whether the effector cell kills the target cell, whether the effector cell releases antibodies, cytokines or other substances that are able to interact with the target cell or are released in the presence of the target cell, or the like.

Certain aspects are generally directed to systems and methods for determining and/or isolating cells (e.g., effector cells) with the ability to kill specific target cells. In some embodiments, assays can be used to determine more than one cytokine or secretion, e.g., within a droplet. Certain embodiments of the invention are generally directed to single-cell, high-throughput techniques, and may include more than one assay to determine or identify whether effector cells are able to kill target cells. For example, effector cells with certain activity (e.g., killing activity) against diseased/infected cells may be determined in some embodiments, e.g., with high accuracy. In some embodiments, such techniques may be used to improve the efficacy of adoptive cell therapy or other applications. In addition, in some embodiments, various types of single- and few-cell responses may be studied.

In some embodiments, two or more cells are contained within a droplet, e.g., a microfluidic droplet. For example, one cell may be an effector cell while the other cell may be a cell suspected of being able to interact (positively or negatively) with the effector cell. For example, the target cell may be a cancer cell, an infected cell, or the like. In addition, in some cases, more than one target cell may be present, and such cells may independently be the same or different. Also, in some embodiments, more than one effector cell may be present, and such cells may independently be the same or different. In some cases, one, two, or more assays are applied to the droplet to determine whether the effector cell and the target cell have interacted in some fashion. For example, one assay may be directed to a "killing assay," i.e., determining whether the target cell is alive or dead through interaction with the effector cell, while another assay may be a cytokine-secretion assay, i.e., determining whether the effector cell has secreted a cytokine. Examples of killing assays include target cell release of a live-dye, activation of an apoptosis indicator, entrance of a death-indicating dye, etc., or other assays described herein. In some cases, two or more assays may be combined, and the droplets sorted on the basis of the results of the assay. For instance, droplets may be sorted when a cytokine release event and a functional killing event both are present within a droplet. Thus, drops containing live cells with the ability to kill target cells may be isolated in certain embodiments.

Examples of applications using such techniques include, but are not limited to, analysis, where one can observe cytokine secretion and cell killing, e.g., dynamically, from a very large number of individual cells, e.g., to study the correlation between cytokine secretion, killing, and transcription. Another example is the isolation of living, target-specific T cells from a subject. These cells may in some cases be expanded in number in vitro, and then injected into the subject, for instance, for adoptive cell therapy or other therapies. As another example, such techniques may be used to identify the T cell receptors that recognize cancer/infected cells, and/or identify the peptide targets that these T cell receptors recognize. This may, for example, be used to determine T cell receptors and their targets, by performing a functional assay while keeping the cells paired in droplets.

In some cases, time course experiments may be performed. For example, a population of droplets containing effector and target cells, beads to assay three different cytokines, and cell-death indicating reagents may be prepared and observed over time, e.g., to determine the time sequence of immune cell activation. For instance, the order in which the cytokines are released and the timing of actual cell killing events may be determined in some cases. As other examples, droplets may be analyzed by cytometric techniques, or droplets in a microfluidic device can be passed through a microscope imaging plane, for example, through light-sheet microscopy, and imaged by fluorescence microscopy. In yet another example, modulation experiments may be performed where many effector cell-target cell functions and cell states are analyzed, e.g., to determine molecules that are able to modulate the immune response. For example, immune-response activators (e.g., for cancer treatments) or immune-response inhibitors (e.g., for autoimmune diseases) may be determined in various embodiments.

In one aspect, the present invention is generally directed to containing, in a droplet, two (or more) cells that are able to interact with each other. For instance, one cell may be an effector cell such as an immune cell, while the other cell may be a target cell such as a cancer cell. Various assays may be conducted to determine an interaction between the two cells; for example, the assays may include a first assay that determines viability of the target cell (e.g., whether the cell is alive or dead), and a second assay that determines a species released by the effector cell (e.g., a cytokine or an antibody). Other assays are discussed in more detail below. In some embodiments, only two cells (one effector cell and one target cell) may be contained within a droplet, e.g., so that specific cell-cell interactions can be determined, although in certain cases, a plurality of microfluidic droplets may be used, some or all of which will contain only two cells.

In some cases, the cells contained within the droplet may interact in some fashion. For instance, one of the cells may act on other cells within the droplet. Droplets where a certain result occurs (e.g., a cell is killed by another cell) may be separated from droplets where other results (or no result) occur. The cells contained within the separated droplets may then be determined or analyzed, for example, by sequencing the cells' DNA, analyzing cellular mRNA levels, analyzing cell protein modifications, e.g., protein phosphorylation levels, etc.

For example, in one set of embodiments, two (or more) cells are contained within a droplet. The cells may arise from the same organism, different organisms of the same species, different organisms of different species (e.g., human and mouse cells, human and rat cells, human cells and bacteria, human cells and fungal cells, rat cells and fungal cells, bacteria and fungal cells, etc.), or the like. The cells may also be genetically modified, for example, a set of cells may be transformed with a library of DNA plasmids that encode potentially functional peptides or proteins. If more than two cells are present in the droplet, some of the cells may be substantially the same (e.g., duplicate cells), and/or there may be three, four, or more types of cells contained within the droplet, and such cells may independently arise from the same species or different species, and from the same organism or different organisms. The cells may be present in a liquid which is then formed into droplets containing the cells, and/or cells may be inserted or injected into the droplets after formation of the droplets. Examples of techniques for containing cells in droplets include those disclosed in Int. Pat. Apl. No. PCT/US2004/027912, filed Aug. 27, 2004, entitled "Electronic Control of Fluidic Species," by Link, et al., published as WO 2005/021151 on Mar. 10, 2005, or Int. Pat. Apl. No. PCT/US2010/040006, filed Jun. 25, 2010, entitled "Fluid Injection," by Weitz, et al., published as WO 2010/151776 on Dec. 29, 2010, each incorporated herein by reference in its entirety. Other techniques known to those of ordinary skill in the art for producing a cell contained within a droplet may also be used.

In some cases, one (or more) of the cells may be an effector cell that interacts with other cells (e.g., a target cell) to produce a change in the target cell (and/or in some cases, the effector cell). For example, the effector cell may be a T-cell or other immune cell that recognizes a target cell, e.g., the T-cell may kill or inhibit the target cell. As another example, the effector cell may be a cell that secretes a substance (e.g., a cytokine, a growth factor, a neurotransmitter, a hormone, a signaling peptide or other signaling compound, an apoptosis inducing factor, etc.), that influences the target cell in a determinable way (e.g., by inhibiting or promoting cell growth, division, apoptosis, differentiation, etc.). In some cases, the target cell and/or the effector cell may be genetically modified, e.g., to produce or increase production of the secreted substance, although in other cases, the cells are not genetically modified.

In addition in some cases, the effector cell may be genetically modified or engineered. For example, in one set of embodiments, the effector cell may be a T cell having a genetically-modified T cell receptor. For instance, in some cases, a T-cell may be taken from a subject (e.g., healthy or diseased), and modified to include a chimeric antigen receptor. The T-cells may be expanded, then assayed as discussed herein to determine target cells that the modified T-cells react to.

In some embodiments, the effector cells may interact with the target cells by producing or secreting antibodies, cytokines, or cytolytic proteins, or other compounds (e.g., perforins, granzymes, etc.) that are able to interact with the target cell. Other compounds that could be secreted include other gene-encoded proteins or other compounds that are not proteins, e.g., penicillins, hormones, small molecules (e.g. less than 2 kDa or 1 kDa), etc. As another example, the effector cells may kill the target cells, e.g., through phagocytosis, inducement of apoptosis, etc. The effector cells may also release signaling molecules or other substances that interact with the target cell, as mentioned above. Examples of effector cells include, but are not limited to, immune cells such as B-cells, T-cells, natural killer cells, lymphocytes, macrophages, neutrophils, basophils, mast cells, or the like. In one set of embodiments, for instance, the effector cell is a CD8+ T-cell. Non-limiting examples of target cells include cancer cells (or cells suspected of being cancerous), normal cells, foreign cells (e.g., bacteria, fungi, pathogens, etc.), viruses, or the like. In some cases, the target cell may be an infected cell, e.g., a cell infected with a bacterium, a virus, a fungus, a pathogen, or the like. As mentioned, the interaction between the effector cell and the target cell may be direct (e.g., the effector cell binds directly to the target cell), and/or indirect (e.g., the target cell may secrete a substance that affects the target cell). As non-limiting examples, T-cells and tumor cells from a cancer patient could be studied to determine those receptors on the T-cells that are able to recognize such tumor cells, or a T-cell may be associated with cells infected with a pathogen (e.g., a bacterium or a virus) to determine those receptors able to recognize the pathogen.

The cells may arise from any suitable species, and as mentioned, cells from more than one species may be present within a droplet. For example, effector cells and target cells may come from the same species or different species. The cells may include a eukaryotic cell, an animal cell, a plant cell, a bacterium or other single-cell organism, etc. If the cell is an animal cell, the cell may be, for example, an invertebrate cell (e.g., a cell from a fruit fly), a fish cell (e.g., a zebrafish cell), an amphibian cell (e.g., a frog cell), a reptile cell, a bird cell, or a human or non-human mammal, such as a monkey, ape, cow, sheep, goat, horse, rabbit, pig, mouse, rat, guinea pig, dog, cat, etc. If the cell is from a multicellular organism, the cell may be from any part of the organism. For instance, if the cell is from an animal, the cell may be an immune cell, a cardiac cell, a fibroblast, a keratinocyte, a heptaocyte, a chondracyte, a neural cell, an osteocyte, an osteoblast, a muscle cell, a blood cell, an endothelial cell, or the like. In some cases, the cell is genetically engineered.

In some cases, the target cell may contain or be exposed to a signaling entity. The signaling entity may be any entity that can be determined in some fashion using a detection method. For example, the signaling entity may be a fluorescent entity that is released from the target cell upon death or rupture of the target cell, or the signaling entity may be an inhibitor of a fluorescent signal. Thus, the droplets can be determined to determine the signaling entity (e.g., by determining fluorescence). For example, the distribution and/or intensity of the signaling entity may be determined within the droplet, and the droplet sorted on the basis of the signaling entity. Examples of sorting techniques are discussed in more detail below. For example, viability of target cells may be determined by determining leakage of signaling entity from the target cells, and the cells sorted based on such determinations. As another example, a state or characteristic of the target cell (e.g., its internal pH or its size) may be determined using the signaling entity. As another example, the target cell may respond to a signaling entity by synthesizing a measurable species, such as a particular mRNA or protein. In some cases, the measurable synthesized protein may be a marker protein such as Green Fluorescent Protein (GFP).

For example, in some embodiments, the target cell and/or the effector cell may be exposed to a signaling entity that determines cell viability. In some cases, the signaling entity may signal when a cell is alive, or in other cases, the signaling entity may signal when a cell is dead. Examples of such signaling entities include, but are not limited to, SYTOX® Orange, eFluor® 455UV, eFluor® 450, eFluor® 506, eFluor® 520, eFluor® 660, eFluor® 780, calcein, a calcein derivative (e.g., Calcein AM, Calcein Violet AM, Calcein Blue AM), propidium iodide, 7-AAD (7-aminoactinomycin D), Live/Dead®, propidium iodide, trypan blue, resazurin, formazan, ethidium homodimer, Evans blue, fluorescein diacetate, formazan (MTT/XTT), lactate dehydrogenase, methyl violet, or the like, as well as combinations of these and or other suitable viability signaling entities. By determining the signaling entity within the droplet, e.g., by determining a location, color, etc. of the signaling entity within the droplet, the state of a cell (e.g., alive or dead) can be determined. In some cases, a droplet may thus be sorted, at least in part, on the basis of the viability of the cell in the droplet.

In addition, in some embodiments, a cytokine or other substance secreted into the droplet (e.g., by the effector cell) may be determined. In some cases, the determination may use a signaling entity, e.g., one that is distinguishable from other signaling entities (e.g., a cell viability signaling entity). For instance, the signaling entities may be distinguishable based on color, fluorescence, intensity, or the like.

For example, in one set of embodiments, a cytokine or other substance (e.g., an antibody, cytolytic protein, perforin, granzyme, or other compound such as is discussed herein) may be determined using a particle having a first antibody on its surface to the cytokine or other substance, and a second, labeled antibody that is also able to bind to the cytokine or other substance. For instance, the second, labeled antibody may be labeled with a fluorescent entity or other signaling entity. If the cytokine (or other substance) is present, then the second, labeled antibody may be able to bind via the cytokine to the particle. Accordingly, detection of the distribution of fluorescence within the droplet may be relatively evenly distributed, or concentrated around particles, which may be indicative of whether the cytokine (or other substance) is present. In some cases, the amount or concentration of cytokine (or other substance) may be determined. Examples of cytokines that may be determinable include, but are not limited to, TNF-alpha (TNF-α) or IFN-gamma (IFN-γ). Other examples of suitable cytokines include lymphokines, interleukins, chemokines, interferons, colony stimulating factors, or the like. Many antibodies to cytokines such as these or others can be readily obtained commercially.

In some cases, cell viability may be determined by determining a product released from the cell. For example, a biomarker such as lactate dehydrogenase may be released by damaged cells, which may be detected using a suitable signaling entity. Kits for determining lactate dehydrogenase released from cells may be obtained commercially (e.g., determined using a colorimetric assay or other suitable signaling entity). In some cases, the biomarker may be an enzyme that can react with a substrate in some way, which may facilitate determination. For example, a biomarker such as lactate dehydrogenase may interact with a suitable substrate, e.g., lactate, and in some cases may convert the substrate into an insoluble product, or a product that can be trapped in a gel (for example in a gel droplet). In addition, other biomarkers may be released from the target cell and/or the effector cell that can be detected using a suitable signaling entity. Non-limiting examples include cyclophilin A (CypA), HSP gp96, calreticulin, hsp90, and hsp70. Antibodies for these may be readily obtained commercially.

The particle (or bead) may include, for example, polystyrene, polyethylene, or any other suitable polymer. In some cases, the particle may be a polymer-coated particle such as polystyrene coated gold particle, polyethylene coated silica particle etc. In some embodiments, the particle may be a gel particle or a hydrogel particle. The particle may be spherical or nonspecial, and may be of any suitable size, e.g., less than about 10 micrometers, less than about 3 micrometers, less than about 1 micrometer, less than about 300 nm, less than about 100 nm, etc. In some cases, the particle may be modified to promote attachment of antibodies or other agents to the surface of the particle. For instance, in one set of embodiments, the particle may be coated with streptavidin and the antibody modified with a biotinylated portion that can bind to the streptavidin, thereby immobilizing the antibody relative to the surface of the particle. Those of ordinary skill in the art will know of other methods of attaching an antibody to a particle.

In some cases, the particle may be optically active particles, and/or coated with a layer of optically active films or nanoparticles. For instance, in one set of embodiments, the particle can be a polystyrene coated gold particle; for example, in some cases, the gold particle resonance wave-length may be matched to the fluorescent spectra to enhance the fluorescent signal. In another set of embodiment, a particle may have a core that is silver-coated silica with the core-shell particle. For instance, the particle may have a polystyrene coating. In some cases, the particle may have a resonance spectrum that is tuned to a wide optical range, thus allowing the enhancement of multiple fluorescent signals.

In some cases, the particles may be able to capture and detect several different molecules simultaneously (e.g., molecules secreted or otherwise released by one or more of target or effector cells). For example, the capture particles can be coated with anti-IFN-gamma antibodies and/or anti-lactose dehydrogenase antibodies in one embodiment. As a specific non-limiting example, the droplets can include a capture particle, effector and target cells, and anti-IFN-gamma antibodies labeled with a first signaling entity (e.g., a fluorescent red dye) and anti-lactose dehydrogenase antibodies labeled with a second signaling entity (e.g., a fluorescent green dye); IFN-gamma is secreted by activated T cells, and lactose dehydrogenase is secreted by damaged/killed cells. A particle that contains both signaling entities (e.g., the particle may be both fluorescent green and fluorescent red) may thus indicate that the T cell was activated, and that one of the two cells within the drop was damaged or killed. This dual signaling may allow, for example, more stringent selection of droplets in which an activated T cell resulted in damage or killing of the target cell; which may provide the ability to distinguish droplets in which the target cell was not killed.

In some embodiments, droplets or gels may be transferred to a solution containing an enzyme-conjugated detection antibody, e.g., an anti-IFN-gamma antibody conjugated to horseradish peroxidase (HRP). After washing the gels to remove unbound detection antibody, a suitable substrate for HRP can be added to the gels (for example, chromogenic or chemiluminescent substrates such as luminol, homovanillic acid, AmplexRed, 3,3',5,5'-tetramethylbenzidine, 3,3'-diaminobenzidine, 2,2'-azino-bis(3-ethylbenzothiazoline-6-sulphonic acid, or the like). The substrate may diffuse into the gels, where it may be converted into an insoluble, colored precipitate by the IFN-gamma-bound HRP-conjugated detection antibody. This colored precipitate can be determined, allowing for collection or solting of the desired hydrogels. In this way, an enzyme-mediated signal amplification can be achieved, which may allow for detection of low concentrations of the secreted molecule of interest.

The second, labeled antibody may be labeled with a fluorescent entity or other signaling entity. For instance, the signaling entity may be a dye, a radioactive atom or compound, etc. The signaling entity may also be an ultraviolet dye or an infrared dye in some cases. Examples of signaling entities include, but are not limited to, calcein (or calcein derivatives such calcein AM), propidium iodide, 7-aminoactinomycin D, nuclear stains, Calcein Blue AM, Calcein Violet AM, Fura-2 AM, Indo-1 AM, resazurin, and the like. Many such dyes are commercially available.

Determination of signaling entity such as those described herein may occur using techniques such as radioactivity, fluorescence, phosphorescence, light scattering, light absorption, fluorescence polarization, or the like. Many detectors that operate using such principles are commercially available. The detector may be used to determine at least one of the signaling entities that may be present, and in some cases, more than one detector may be used.

In some cases, at least about 30%, at least about 40%, at least about 50%, at least about 60%, at least about 70%, at least about 75%, at least about 80%, at least about 85%, at least about 90%, or at least about 95% of the effector cells that are studied within a droplet (or within a population of droplets) are the same type of cell. In some cases, at least about 30%, at least about 40%, at least about 50%, at least about 60%, at least about 70%, at least about 75%, at least about 80%, at least about 85%, at least about 90%, or at least about 95% of the target cells within a droplet (or within a population of droplets) are the same type of cell. However, in other embodiments, populations of target and/or effector cells may be studied. A single type of effector cell may be studied against a range of different types of target cells, or a single target cell may be tested against a range of different types of effector cells, for instance. As non-limiting examples, the target cells may arise from one or more organs from a single organism, and/or from different organisms of the same or different species. In other examples, the target cells may arise from a population of different bacteria or other organisms, e.g., from an infection, a tumor, a soil sample, a water sample, etc.

In one set of embodiments, as a non-limiting example, a droplet can be formed containing a T-cell (or other effector cell), and a cancer cell (or other target cell). In some cases, the droplet may contain a first signaling entity and a second signaling entity distinguishable from the first signaling entity. The cells may be allowed to interact. The droplet may then be analyzed to determine its fluorescence. For example, the first signaling entity may be determined to determine the viability of the target cell, and the second signaling entity may be determined to determine the presence of cytokines, antibodies, or other substances. Based on these determinations, the droplets may be sorted, e.g., such that droplets containing effector cells able to interact with the target cells (positively or negatively) are selected or sorted over droplets containing cells that poorly interact, or do not interact at all. The sorted effector cells may then be analyzed using any suitable technique. For example, the effector cells may be sequenced using techniques known to those of ordinary skill in the art, for example to identify receptors that allowed the cells to recognize the target cells, to identify cytokine sequences that may be present, or the like.

In some embodiments, the droplets may be formed into gels, e.g., such that the cells are encapsulated in a gel, e.g., an agarose gel, a polyacrylamide gel, an alginate gel, or the like. For example, cells may be contained within droplets containing alginate (or other gel precursor) and then the droplets can be converted into alginate hydrogels (or other suitable gels), e.g., by causing the alginate to form a gel (for instance, by exposure to $Ca^{2+}$). The gels can contain, for example, capture particles and detection reagents as described herein with respect to droplets. In some cases, the gel particles may be transferred into a solution (e.g., suspended), and/or analyzed and sorted using flow cytometry (e.g., fluorescence activated cell sorting or FACS) and/or other suitable techniques. In some cases, the gel itself can be modified, for example, by covalent attachment of antibodies, so that secreted molecule are captured by the alginate matrix, rather than a bead. Fluorescent detection antibodies may be used in some embodiments to detect captured analytes, e.g., in gels.

Figure 8:
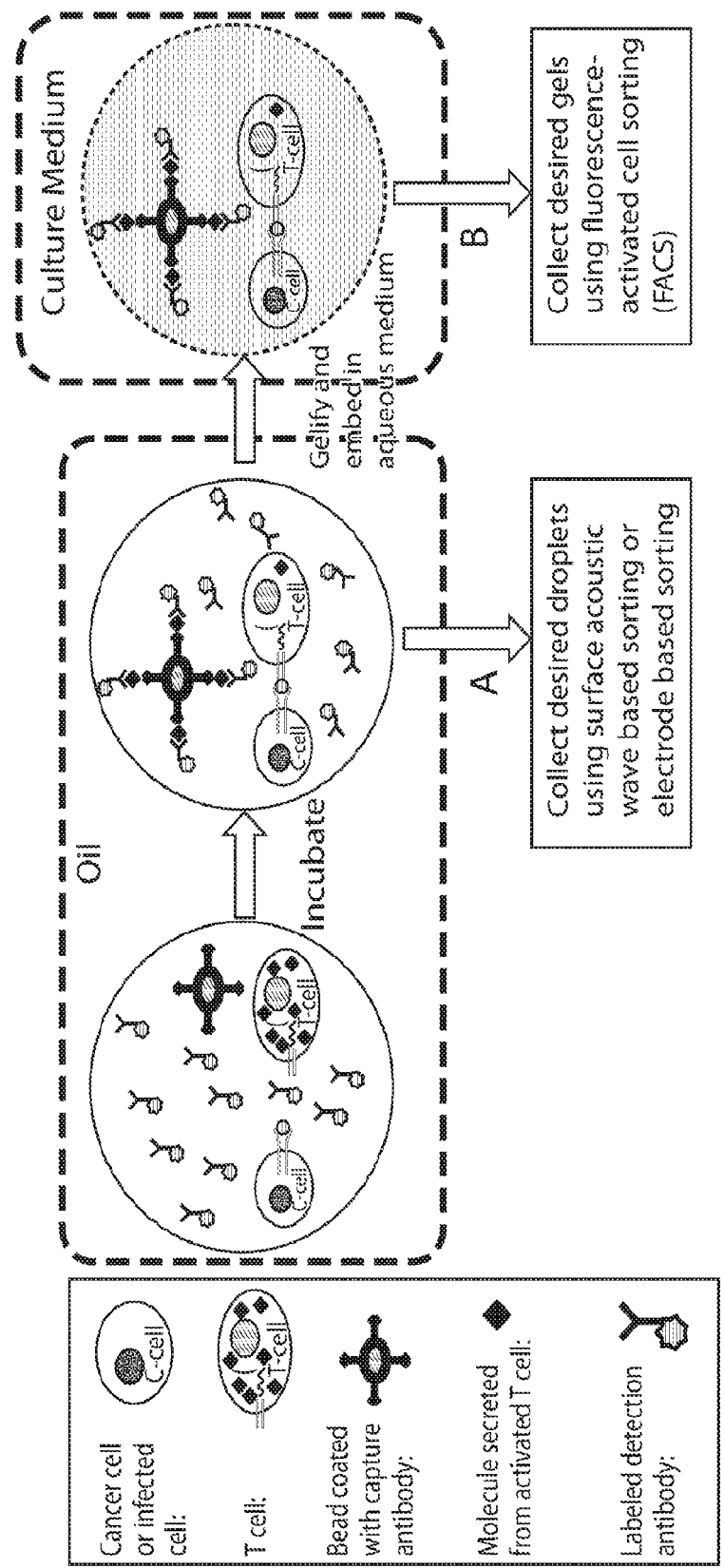
FIG. 8 illustrates encapsulation of cells in droplets or gels, in another embodiment of the invention.

One non-limiting example can be seen in FIG. 8. This figure illustrates cell-cell interaction assays sorted as droplets or gels. Single effector and target cells were first encapsulated into droplets and incubated such that they started signaling. After the secreted molecules were captured onto particles, a droplet sorting device was used to detect and sort desired droplets. In another embodiment, alginate was included in the droplets such that after incubation, the alginate could be gelled and the gels transferred into an aqueous medium. The gels can then be analyzed and sorted, for example, using Fluorescence Activated Cell Sorting (FACS), or other techniques. Non-limiting examples of sorting techniques that may be used, as shown in this figure, include FACS, surface acoustic wave based sorting, or electrode-based sorting (or other sorting techniques using electrical fields). See, for example, U.S. Pat. Apl. Pub. Nos. 2007/0003442, 2013/0213488, or 2014/0305799, each incorporated herein by reference in its entirety. Other examples of techniques useful for sorting or otherwise manipulating cells include those disclosed in U.S. Pat. Apl. Pub. Nos. 2006/0163385, 2015/0283546, 2016/0129444, or 2016/0201129, each incorporated herein by reference in its entirety.

In one set of embodiments, cells sorted for a desired characteristic (e.g., ability to interact with a target cell) may be analyzed to determine various characteristics of the cells. For example, receptors on the cells may be determined or sequenced, e.g., to determine receptors able to interact with the target cells. As other examples, sequences encoding antibodies that are able to interact with the target cells, and/or sequences encoding substances that are secreted to interact with the target cells, may be analyzed. In some cases, all, or a portion of, the DNA or the genome of the effector cells may be sequenced or otherwise determined. The cells may also be grown or expanded (e.g., in number) before such determination, in some embodiments, e.g., using cell culture techniques known to those of ordinary skill in the art. In some cases, the cells that are sorted may be purified and cultured, e.g., for applications as discussed herein, for subsequent study, or for other applications or uses.

The DNA from the cell may be sequenced using any suitable technique known to those of ordinary skill in the art. Examples of DNA sequencing techniques include, but are not limited to, PCR (polymerase chain reaction), "sequencing by synthesis" techniques (e.g., using DNA synthesis by DNA polymerase to identify the bases present in the complementary DNA molecule), "sequencing by ligation" (e.g., using DNA ligases), "sequencing by hybridization" (e.g., using DNA microarrays), nanopore sequencing techniques, or the like. Optionally, the extracted nucleic acid sequence may be amplified, duplicated, or expanded by PCR, rolling circle replication, or other techniques known to those of ordinary skill in the art.

In some embodiments, assays may be used to assess target recognition and/or killing activity of one or several or many effector cells. As discussed herein, droplets can be created, analyzed, and sorted at high rates (hundreds to thousands per second). Multiple assays (e.g., cytokine secretion, cell killing, identification of activation marker, etc.) can also be performed with the same droplet, which minimize noise or isolation of cells that happen to be dying or releasing cytokines at the time of encapsulation before any cell-cell interaction can happen, or other false-positive events. In some cases, after the droplets of interest are sorted, the effector cells may still be viable and, for example, can be released to expand cell number.

In some embodiments, the droplets can be sorted and then genes or transcripts of the encapsulated cells can be sequenced. For example, upregulation of apoptosis-related genes, may be used to determine, confirm, or study killing of the target cell. In some cases, the sequences of cell receptors from the effector cells can also be identified. Nucleic acid analysis of sorted droplets may also reveal, in some cases, certain features of the target cell, for example type, behavior, physiology, condition, etc.

As mentioned, the sequencing can be performed by any suitable technique. For example, droplets of interest can be dispensed into wells and then sequenced by Sanger methods, and the effector and target cell information will remain paired in the well. As another example, droplet-based barcoding can be used, which will maintain droplet-pairing of effector and target cells during next-generation sequencing. See, for example, U.S. Pat. Apl. Pub. No. 2015-0298091, incorporated herein by reference in its entirety. For example, droplets may be broken (e.g., using mechanical disruption, ultrasound, chemical agents, or surfactants, for example, 1H,1H,2H,2H-perfluorooctanol) and their contents merged together for sequencing or other purposes.

In some embodiments, the nucleic acids may be sequenced using a variety of techniques and instruments, many of which are readily available commercially. Examples of such techniques include, but are not limited to, chain-termination sequencing, sequencing-by-hybridization, Maxam-Gilbert sequencing, dye-terminator sequencing, chain-termination methods, Massively Parallel Signature Sequencing (Lynx Therapeutics), polony sequencing, pyrosequencing, sequencing by ligation, ion semiconductor sequencing, DNA nanoball sequencing, single-molecule real-time sequencing, nanopore sequencing, microfluidic Sanger sequencing, digital RNA sequencing ("digital RNA-seq"), etc.

In some cases, the assay may determine cell cytokine secretion at a single cell level. In some cases, picoliter or microfluidic droplets may be helpful since the concentration of cytokines in droplets with single-cell secretion can easily reach a few nanomolar after one or two hours of incubation. In contrast, cytokines secreted from single cells in bulk solutions are not easily detectable with current methods.

In addition, in some embodiments, two or more cell signals or functions may be determined. In some cases, a bead-based assay can be used to determine effector cell response to a target cell, and can be used in conjunction with other assays, e.g., methods to indicate cell vitality, cell death, etc. A combination of assays outputs can reduce false-positives significantly.

In addition, in certain embodiments, rapid selection of effector cells may be performed at high accuracy, and may significantly improve activity and efficacy of cells isolated for adoptive cell therapy or other applications. For example, in some cases, effector cells from a subject may be assayed and sorted based on interactions with target cells as discussed above, then the sorted effector cells may be expanded and re-introduced into the subject (or to another subject), e.g., for therapeutic purposes.

In some embodiments, effectors cells may be identified and sorted without any tagging on the cell surface, e.g., resulting in a population of tag-free effector cells, which may improve the efficacy of cells for adoptive cell therapy or other applications. For example, in some cases, effectors T cells are assayed by a secretion capturing bead and the death of a cancer cell, instead of through fluorescent tagging of activation markers on the T-cell surface, which may incur cytotoxicity.

In some aspects, relatively large numbers of droplets may be created that contain the same type and/or numbers of cells therein. For example, a population of at least 10, at least 30, at least 50, at least 100, at least 300, at least 500, at least 1,000, at least 3,000, at least 5,000, at least 10,000, at least 30,000, at least 50,000, at least 100,000 droplets, at least 300,000 droplets, at least 500,000 droplets, at least 1,000, 000 droplets, at least 3,000,000 droplets, at least 5,000,000 droplets, at least 10,000,000 droplets, etc., containing cells (e.g., one or more effector cells and/or one or more target cells) may be created. In some cases, at least about 30%, at least about 40%, at least about 50%, at least about 60%, at least about 70%, at least about 75%, at least about 80%, at least about 85%, at least about 90%, or at least about 95% of the droplets that are created may contain the same number of cells (e.g., 2 cells), and/or the same number of types of cells (e.g., a particular effector cell and a particular target cell). For example, the droplets may each contain at least one immune cell and at least one target cell (e.g., a cancer cell or an infected cell) for the immune cell.

As mentioned, various aspects of the invention relates to systems and methods for producing droplets of fluid surrounded by a liquid. Any technique may be used to make a droplet, including those described herein. The fluid and the liquid may be essentially immiscible in many cases, i.e., immiscible on a time scale of interest (e.g., the time it takes a fluidic droplet to be transported through a particular system or device). In certain cases, the droplets may each be substantially of the same shape or size, as described herein. The fluid may also contain other species, for example, certain molecular species (e.g., as discussed herein), cells, particles, etc.

In one set of embodiments, for example, electric charge may be created on a fluid surrounded by a liquid, which may cause the fluid to separate into individual droplets within the liquid. In some embodiments, the fluid and the liquid may be present in a channel, e.g., a microfluidic channel, or other constricted space that facilitates application of an electric field to the fluid (which may be "AC" or alternating current, "DC" or direct current etc.), for example, by limiting movement of the fluid with respect to the liquid. Thus, the fluid can be present as a series of individual charged and/or electrically inducible droplets within the liquid. In one embodiment, the electric force exerted on the fluidic droplet may be large enough to cause the droplet to move within the liquid. In some cases, the electric force exerted on the fluidic droplet may be used to direct a desired motion of the droplet within the liquid, for example, to or within a channel or a microfluidic channel (e.g., as further described herein), etc.

Electric charge may be created in the fluid within the liquid using any suitable technique, for example, by placing the fluid within an electric field (which may be AC, DC, etc.), and/or causing a reaction to occur that causes the fluid to have an electric charge, for example, a chemical reaction, an ionic reaction, a photocatalyzed reaction, etc. In one embodiment, the fluid is an electrical conductor. As used herein, a "conductor" is a material having a conductivity of at least about the conductivity of 18 megohm (MOhm or MΩ) water. The liquid surrounding the fluid may have a conductivity less than that of the fluid. For instance, the liquid may be an insulator, relative to the fluid, or at least a "leaky insulator," i.e., the liquid is able to at least partially electrically insulate the fluid for at least a short period of time. Those of ordinary skill in the art will be able to identify the conductivity of fluids. In one non-limiting embodiment, the fluid may be substantially hydrophilic, and the liquid surrounding the fluid may be substantially hydrophobic.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments. As used herein, "integral" means that portions of the components integral to each other are joined in such a way that the components cannot be manually separated from each other without cutting or breaking at least one of the components.

In an additional set of embodiments, for example, mechanical force such as an acoustic force may be used to create and/or manipulate droplet. In some cases, an electromechanical actuation may be embedded on a chip and a mechanical valve can be open and closed periodically to allow the flow of the liquid to make droplets. See, e.g., Int. Pat. Apl. Pub. Nos. WO 2012/027366, WO 2014/066624, or WO 2015/200616, each of which is incorporated herein by reference in its entirety.

In another set of embodiments, droplets of fluid can be created from a fluid surrounded by a liquid within a channel by altering the channel dimensions in a manner that is able to induce the fluid to form individual droplets. The channel may, for example, be a channel that expands relative to the direction of flow, e.g., such that the fluid does not adhere to the channel walls and forms individual droplets instead, or a channel that narrows relative to the direction of flow, e.g., such that the fluid is forced to coalesce into individual droplets. In other embodiments, internal obstructions may also be used to cause droplet formation to occur. For instance, baffles, ridges, posts, or the like may be used to disrupt liquid flow in a manner that causes the fluid to coalesce into fluidic droplets.

In some cases, the channel dimensions may be altered with respect to time (for example, mechanically or electromechanically, pneumatically, etc.) in such a manner as to cause the formation of individual fluidic droplets to occur. For example, the channel may be mechanically contracted ("squeezed") to cause droplet formation, or a fluid stream may be mechanically disrupted to cause droplet formation, for example, through the use of moving baffles, rotating blades, or the like. Other examples of methods for creating droplets include those disclosed in Int. Pat. Apl. No. PCT/US2003/020542, filed Jun. 30, 2003, entitled "Method and Apparatus for Fluid Dispersion," by Stone, et al., published as WO 2004/002627 on Jan. 8, 2004.

In some instances, the droplets may be created at relatively high rates. For instance, at least about 1 droplet per second may be created in some cases, and in other cases, at least about 10 droplets per second, at least about 20 droplets per second, at least about 30 droplets per second, at least about 100 droplets per second, at least about 200 droplets per second, at least about 300 droplets per second, at least about 500 droplets per second, at least about 750 droplets per second, at least about 1000 droplets per second, at least about 1500 droplets per second, at least about 2000 droplets per second, at least about 3000 droplets per second, at least about 5000 droplets per second, at least about 7500 droplets per second, at least about 10,000 droplets per second, at least about 15,000 droplets per second, at least about 20,000 droplets per second, at least about 30,000 droplets per second, at least about 50,000 droplets per second, at least about 75,000 droplets per second, at least about 100,000 droplets per second, at least about 150,000 droplets per second, at least about 200,000 droplets per second, at least about 300,000 droplets per second, at least about 500,000 droplets per second, at least about 750,000 droplets per second, at least about 1,000,000 droplets per second, at least about 1,500,000 droplets per second, at least about 2,000,000 or more droplets per second, or at least about 3,000,000 or more droplets per second may be created.

Other examples of the production of droplets of fluid surrounded by a liquid are described in International Patent Application Serial No. PCT/US2004/010903, filed Apr. 9, 2004 by Link, et al., and International Patent Application Serial No. PCT/US03/20542, filed Jun. 30, 2003 by Stone, et al., published as WO 2004/002627 on Jan. 8, 2004, each incorporated herein by reference.

In some embodiments, a species (for example, a cell) may be contained within the droplet, e.g., before or after formation. In some cases, more than one species may be present. Thus, for example, a precise quantity of a drug, pharmaceutical, or other agent can be contained within a droplet, e.g., in addition to a cell. For example, the species may be drug or other species that is suspected of being able to affect the interaction between an effector cell and a target cell within a droplet. Other species that can be contained within a droplet include, for example, biochemical species such as nucleic acids such as siRNA, mRNA, RNAi and DNA, proteins, peptides, or enzymes, or the like. Additional species that can be contained within a droplet include, but are not limited to, nanoparticles, quantum dots, proteins, indicators, dyes, fluorescent species, chemicals, amphiphilic compounds, detergents, drugs, or the like. Further examples of species that can be contained within a droplet include, but are not limited to, growth regulators, vitamins, hormones, or microbicides.

In certain instances, the invention provides for the production of droplets consisting essentially of a substantially uniform number of entities of a species therein (i.e., molecules, cells, particles, etc.). For example, about 90%, about 93%, about 95%, about 97%, about 98%, or about 99%, or more of a plurality or series of droplets may each contain the same number of entities of a particular species. For instance, a substantial number of fluidic droplets produced, e.g., as described above, may each contain 1 entity, 2 entities, 3 entities, 4 entities, 5 entities, 7 entities, 10 entities, 15 entities, 20 entities, 25 entities, 30 entities, 40 entities, 50 entities, 60 entities, 70 entities, 80 entities, 90 entities, 100 entities, etc., where the entities are molecules or macromolecules, cells, particles, etc. In some cases, the droplets may each independently contain a range of entities, for example, less than 20 entities, less than 15 entities, less than 10 entities, less than 7 entities, less than 5 entities, or less than 3 entities in some cases.

As discussed, in some aspects, fluidic droplets may be screened and/or sorted, and in some cases, at relatively high rates. For example, a characteristic of a droplet may be sensed and/or determined in some fashion (e.g., as herein described), then the droplet may be directed towards a particular region of the device, for example, for sorting or screening purposes. For example, the fluidic droplets may be sorted into two or more than two channels, e.g., based on interaction of the cells within the droplets. In some embodiments, a characteristic of a fluidic droplet may be sensed and/or determined in some fashion, for example, as described herein (e.g., fluorescence of the fluidic droplet may be determined), and, in response, an electric field may be applied or removed from the fluidic droplet to direct the fluidic droplet to a particular region (e.g. a channel). Other techniques for sensing cells and/or for sorting cells that are known to those of ordinary skill in the art may also be used, in some embodiments of the invention.

In some cases, high sorting speeds may be achievable using certain systems and methods of the invention. For instance, at least about 1 droplet per second may be determined and/or sorted in some cases, and in other cases, at least about 10 droplets per second, at least about 20 droplets per second, at least about 30 droplets per second, at least about 100 droplets per second, at least about 200 droplets per second, at least about 300 droplets per second, at least about 500 droplets per second, at least about 750 droplets per second, at least about 1000 droplets per second, at least about 1500 droplets per second, at least about 2000 droplets per second, at least about 3000 droplets per second, at least about 5000 droplets per second, at least about 7500 droplets per second, at least about 10,000 droplets per second, at least about 15,000 droplets per second, at least about 20,000 droplets per second, at least about 30,000 droplets per second, at least about 50,000 droplets per second, at least about 75,000 droplets per second, at least about 100,000 droplets per second, at least about 150,000 droplets per second, at least about 200,000 droplets per second, at least about 300,000 droplets per second, at least about 500,000 droplets per second, at least about 750,000 droplets per second, at least about 1,000,000 droplets per second, at least about 1,500,000 droplets per second, at least about 2,000,000 or more droplets per second, or at least about 3,000,000 or more droplets per second may be determined and/or sorted in such a fashion.

In one set of embodiments, a fluidic droplet may be directed by creating an electric charge (e.g., as previously described) on the droplet, and steering the droplet using an applied electric field, which may be an AC field, a DC field, etc. As an example, an electric field may be selectively applied and removed (or a different electric field may be applied, e.g., a reversed electric field) as needed to direct the fluidic droplet to a particular region. The electric field may be selectively applied and removed as needed, in some embodiments, without substantially altering the flow of the liquid containing the fluidic droplet. For example, a liquid may flow on a substantially steady-state basis (i.e., the average flowrate of the liquid containing the fluidic droplet deviates by less than 20% or less than 15% of the steady-state flow or the expected value of the flow of liquid with respect to time, and in some cases, the average flowrate may deviate less than 10% or less than 5%) or other predetermined basis through a fluidic system of the invention (e.g., through a channel or a microchannel), and fluidic droplets contained within the liquid may be directed to various regions, e.g., using an electric field, without substantially altering the flow of the liquid through the fluidic system.

In another set of embodiments, a fluidic droplet may be sorted or steered by inducing a dipole in the fluidic droplet (which may be initially charged or uncharged), and sorting or steering the droplet using an applied electric field. The electric field may be an AC field, a DC field, etc.

In other embodiments, however, the fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc.

In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. The liquid reservoirs may be positioned such that, when activated, the movement of liquid caused by the activated reservoirs causes the liquid to flow in a preferred direction, carrying the fluidic droplet in that preferred direction. For instance, the expansion of a liquid reservoir may cause a flow of liquid towards the reservoir, while the contraction of a liquid reservoir may cause a flow of liquid away from the reservoir. In some cases, the expansion and/or contraction of the liquid reservoir may be combined with other flow-controlling devices and methods, e.g., as described herein. Non-limiting examples of devices able to cause the expansion and/or contraction of a liquid reservoir include pistons and piezoelectric components. In some cases, piezoelectric components may be particularly useful due to their relatively rapid response times, e.g., in response to an electrical signal.

In certain aspects of the invention, sensors are provided that can sense and/or determine one or more characteristics of the fluidic droplets, and/or a characteristic of a portion of the fluidic system containing the fluidic droplet (e.g., the liquid surrounding the fluidic droplet) in such a manner as to allow the determination of one or more characteristics of the fluidic droplets. Characteristics determinable with respect to the droplet and usable in the invention can be identified by those of ordinary skill in the art. Non-limiting examples of such characteristics include fluorescence, spectroscopy (e.g., optical, infrared, ultraviolet, etc.), radioactivity, mass, volume, density, temperature, viscosity, pH, concentration of a substance, such as a biological substance (e.g., a protein, a nucleic acid, etc.), or the like.

In some cases, the sensor may be connected to a processor, which in turn, cause an operation to be performed on the fluidic droplet, for example, by sorting the droplet, adding or removing electric charge from the droplet, fusing the droplet with another droplet, etc. One or more sensors and/or processors may be positioned to be in sensing communication with the fluidic droplet. "Sensing communication," as used herein, means that the sensor may be positioned anywhere such that the fluidic droplet within the fluidic system (e.g., within a channel), and/or a portion of the fluidic system containing the fluidic droplet may be sensed and/or determined in some fashion. For example, the sensor may be in sensing communication with the fluidic droplet and/or the portion of the fluidic system containing the fluidic droplet fluidly, optically or visually, thermally, pneumatically, electronically, or the like. The sensor can be positioned proximate the fluidic system, for example, embedded within or integrally connected to a wall of a channel, or positioned separately from the fluidic system but with physical, electrical, and/or optical communication with the fluidic system so as to be able to sense and/or determine the fluidic droplet and/or a portion of the fluidic system containing the fluidic droplet (e.g., a channel or a microchannel, a liquid containing the fluidic droplet, etc.). For example, a sensor may be free of any physical connection with a channel containing a droplet, but may be positioned so as to detect electromagnetic radiation arising from the droplet or the fluidic system, such as infrared, ultraviolet, or visible light. The electromagnetic radiation may be produced by the droplet, and/or may arise from other portions of the fluidic system (or externally of the fluidic system) and interact with the fluidic droplet and/or the portion of the fluidic system containing the fluidic droplet in such as a manner as to indicate one or more characteristics of the fluidic droplet, for example, through absorption, reflection, diffraction, refraction, fluorescence, phosphorescence, changes in polarity, phase changes, changes with respect to time, etc. As an example, a laser may be directed towards the fluidic droplet and/or the liquid surrounding the fluidic droplet, and the fluorescence of the fluidic droplet and/or the surrounding liquid may be determined. "Sensing communication," as used herein may also be direct or indirect. As an example, light from the fluidic droplet may be directed to a sensor, or directed first through a fiber optic system, a waveguide, etc., before being directed to a sensor.

Non-limiting examples of sensors useful in the invention include optical or electromagnetically-based systems. For example, the sensor may be a fluorescence sensor (e.g., stimulated by a laser), a microscopy system (which may include a camera or other recording device), or the like. As another example, the sensor may be an electronic sensor, e.g., a sensor able to determine an electric field or other electrical characteristic. For example, the sensor may detect capacitance, inductance, etc., of a fluidic droplet and/or the portion of the fluidic system containing the fluidic droplet.

As used herein, a "processor" or a "microprocessor" is any component or device able to receive a signal from one or more sensors, store the signal, and/or direct one or more responses (e.g., as described above), for example, by using a mathematical formula or an electronic or computational circuit. The signal may be any suitable signal indicative of the environmental factor determined by the sensor, for example a pneumatic signal, an electronic signal, an optical signal, a mechanical signal, etc.

As a particular non-limiting example, a device of the invention may contain fluidic droplets containing one or more cells. The cells may be exposed to a signaling entity, such as a fluorescent signal marker that binds if a certain condition is present, for example, the marker may bind to a first cell type but not a second cell type, the marker may bind to an expressed protein, the marker may indicate viability of the cell (i.e., if the cell is alive or dead), the marker may be indicative of the state of development or differentiation of the cell, etc., and the cells may be directed through a fluidic system of the invention based on the presence/absence, and/or magnitude of the fluorescent signal marker. For instance, determination of the fluorescent signal marker may cause the cells to be directed to one region of the device (e.g., a collection chamber), while the absence of the fluorescent signal marker may cause the cells to be directed to another region of the device (e.g., a waste chamber). Thus, in this example, a population of cells may be screened and/or sorted on the basis of one or more determinable or targetable characteristics of the cells, for example, to select live cells, cells expressing a certain protein, a certain cell type, etc.

As mentioned, certain aspects of the invention are directed to the production of droplets using apparatuses and devices such as those described herein, for example, within microfluidic channels or other microfluidic systems. In some cases, e.g., with relatively large numbers of side channels, relatively large droplet production rates may be achieved. For instance, in some cases, greater than about 1,000 droplets/s, greater than or equal to 5,000 droplets/s, greater than about 10,000 droplets/s, greater than about 50,000 droplets/ s, greater than about 100,000 droplets/s, greater than about 300,000 droplets/s, greater than about 500,000 droplets/s, or greater than about 1,000,000 droplets/s, etc. may be produced.

In addition, in some cases, a plurality of droplets may be produced that are substantially monodisperse, in some embodiments. In some cases, the plurality of droplets may have a distribution of characteristic dimensions such that no more than about 20%, no more than about 18%, no more than about 16%, no more than about 15%, no more than about 14%, no more than about 13%, no more than about 12%, no more than about 11%, no more than about 10%, no more than about 5%, no more than about 4%, no more than about 3%, no more than about 2%, no more than about 1%, or less, of the droplets have a characteristic dimension greater than or less than about 20%, less than about 30%, less than about 50%, less than about 75%, less than about 80%, less than about 90%, less than about 95%, less than about 99%, or more, of the average characteristic dimension of all of the droplets. Those of ordinary skill in the art will be able to determine the average characteristic dimension of a population of droplets, for example, using laser light scattering, microscopic examination, or other known techniques. In one set of embodiments, the plurality of droplets may have a distribution of characteristic dimension such that no more than about 20%, no more than about 10%, or no more than about 5% of the droplets may have a characteristic dimension greater than about 120% or less than about 80%, greater than about 115% or less than about 85%, or greater than about 110% or less than about 90% of the average of the characteristic dimension of the plurality of droplets. The "characteristic dimension" of a droplet, as used herein, is the diameter of a perfect sphere having the same volume as the droplet. In addition, in some instances, the coefficient of variation of the characteristic dimension of the exiting droplets may be less than or equal to about 20%, less than or equal to about 15%, or less than or equal to about 10%.

The average characteristic dimension or diameter of the plurality of droplets, in some embodiments, may be less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average characteristic dimension of a droplet (or plurality of droplets) may also be greater than or equal to about 1 micrometer, greater than or equal to about 2 micrometers, greater than or equal to about 3 micrometers, greater than or equal to about 5 micrometers, greater than or equal to about 10 micrometers, greater than or equal to about 15 micrometers, or greater than or equal to about 20 micrometers in certain cases.

In some embodiments, the fluidic droplets may each be substantially the same shape and/or size. The shape and/or size can be determined, for example, by measuring the average diameter or other characteristic dimension of the droplets. The term "determining," as used herein, generally refers to the analysis or measurement of a species, for example, quantitatively or qualitatively, and/or the detection of the presence or absence of the species. "Determining" may also refer to the analysis or measurement of an interaction between two or more species, for example, quantitatively or qualitatively, or by detecting the presence or absence of the interaction.

In some embodiments, a droplet may undergo additional processes. For example, as discussed, a droplet may be sorted and/or detected. For example, a species within a droplet may be determined, and the droplet may be sorted based on that determination. In general, a droplet may undergo any suitable process known to those of ordinary skill in the art. See, e.g., Int. Pat. Apl. No. PCT/US2004/010903, filed Apr. 9, 2004, entitled "Formation and Control of Fluidic Species," by Link, et al., published as WO 2004/091763 on Oct. 28, 2004; Int. Pat. Apl. No. PCT/US2003/020542, filed Jun. 30, 2003, entitled "Method and Apparatus for Fluid Dispersion," by Stone, et al., published as WO 2004/002627 on Jan. 8, 2004; Int. Pat. Apl. No. PCT/US2006/007772, filed Mar. 3, 2006, entitled "Method and Apparatus for Forming Multiple Emulsions," by Weitz, et al., published as WO 2006/096571 on Sep. 14, 2006; Int. Pat. Apl. No. PCT/US2004/027912, filed Aug. 27, 2004, entitled "Electronic Control of Fluidic Species," by Link, et al., published as WO 2005/021151 on Mar. 10, 2005, each of which is incorporated herein by reference in their entireties.

Certain aspects of the invention are generally directed to devices containing channels such as those described above. In some cases, some of the channels may be microfluidic channels, but in certain instances, not all of the channels are microfluidic. There can be any number of channels, including microfluidic channels, within the device, and the channels may be arranged in any suitable configuration. The channels may be all interconnected, or there can be more than one network of channels present. The channels may independently be straight, curved, bent, etc. In some cases, there may be a relatively large number and/or a relatively large length of channels present in the device. For example, in some embodiments, the channels within a device, when added together, can have a total length of at least about 100 micrometers, at least about 300 micrometers, at least about 500 micrometers, at least about 1 mm, at least about 3 mm, at least about 5 mm, at least about 10 mm, at least about 30 mm, at least 50 mm, at least about 100 mm, at least about 300 mm, at least about 500 mm, at least about 1 m, at least about 2 m, or at least about 3 m in some cases. As another example, a device can have at least 1 channel, at least 3 channels, at least 5 channels, at least 10 channels, at least 20 channels, at least 30 channels, at least 40 channels, at least 50 channels, at least 70 channels, at least 100 channels, etc.

In some embodiments, at least some of the channels within the device are microfluidic channels. "Microfluidic," as used herein, refers to a device, article, or system including at least one fluid channel having a cross-sectional dimension of less than about 1 mm. The "cross-sectional dimension" of the channel is measured perpendicular to the direction of net fluid flow within the channel. Thus, for example, some or all of the fluid channels in a device can have a maximum cross-sectional dimension less than about 2 mm, and in certain cases, less than about 1 mm. In one set of embodiments, all fluid channels in a device are microfluidic and/or have a largest cross sectional dimension of no more than about 2 mm or about 1 mm. In certain embodiments, the fluid channels may be formed in part by a single component (e.g. an etched substrate or molded unit). Of course, larger channels, tubes, chambers, reservoirs, etc. can be used to store fluids and/or deliver fluids to various elements or systems in other embodiments of the invention, for example, as previously discussed. In one set of embodiments, the maximum cross-sectional dimension of the channels in a device is less than 500 micrometers, less than 200 micrometers, less than 100 micrometers, less than 50 micrometers, or less than 25 micrometers, less than about 10 micrometers, less than about 5 micrometers, or less than about 1 micrometer.

A "channel," as used herein, means a feature on or in a device or substrate that at least partially directs flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlets and/or outlets or openings. A channel may also have an aspect ratio (length to average cross sectional dimension) of at least 2:1, more typically at least about 3:1, at least about 4:1, at least about 5:1, at least about 6:1, at least about 8:1, at least about 10:1, at least about 15:1, at least about 20:1, at least about 30:1, at least about 40:1, at least about 50:1, at least about 60:1, at least about 70:1, at least about 80:1, at least about 90:1, at least about 100:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. Non-limiting examples of force actuators that can produce suitable forces include piezo actuators, pressure valves, electrodes to apply AC electric fields, and the like. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to net fluid flow of less than about 5 mm or 2 mm, or less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases, the dimensions of the channel are chosen such that fluid is able to freely flow through the device or substrate. The dimensions of the channel may also be chosen, for example, to allow a certain volumetric or linear flow rate of fluid in the channel. Of course, the number of channels and the shape of the channels can be varied by any method known to those of ordinary skill in the art. In some cases, more than one channel may be used. For example, two or more channels may be used, where they are positioned adjacent or proximate to each other, positioned to intersect with each other, etc.

In certain embodiments, one or more of the channels within the device may have an average cross-sectional dimension of less than about 10 cm. In certain instances, the average cross-sectional dimension of the channel is less than about 5 cm, less than about 3 cm, less than about 1 cm, less than about 5 mm, less than about 3 mm, less than about 1 mm, less than 500 micrometers, less than 200 micrometers, less than 100 micrometers, less than 50 micrometers, or less than 25 micrometers. The "average cross-sectional dimension" is measured in a plane perpendicular to net fluid flow within the channel. If the channel is non-circular, the average cross-sectional dimension may be taken as the diameter of a circle having the same area as the cross-sectional area of the channel. Thus, the channel may have any suitable cross-sectional shape, for example, circular, oval, triangular, irregular, square, rectangular, quadrilateral, or the like. In some embodiments, the channels are sized so as to allow laminar flow of one or more fluids contained within the channel to occur.

The channel may also have any suitable cross-sectional aspect ratio. The "cross-sectional aspect ratio" is, for the cross-sectional shape of a channel, the largest possible ratio (large to small) of two measurements made orthogonal to each other on the cross-sectional shape. For example, the channel may have a cross-sectional aspect ratio of less than about 2:1, less than about 1.5:1, or in some cases about 1:1 (e.g., for a circular or a square cross-sectional shape). In other embodiments, the cross-sectional aspect ratio may be relatively large. For example, the cross-sectional aspect ratio may be at least about 2:1, at least about 3:1, at least about 4:1, at least about 5:1, at least about 6:1, at least about 7:1, at least about 8:1, at least about 10:1, at least about 12:1, at least about 15:1, or at least about 20:1.

As mentioned, the channels can be arranged in any suitable configuration within the device. Different channel arrangements may be used, for example, to manipulate fluids, droplets, and/or other species within the channels. For example, channels within the device can be arranged to create droplets (e.g., discrete droplets, single emulsions, double emulsions or other multiple emulsions, etc.), to mix fluids and/or droplets or other species contained therein, to screen or sort fluids and/or droplets or other species contained therein, to split or divide fluids and/or droplets, to cause a reaction to occur (e.g., between two fluids, between a species carried by a first fluid and a second fluid, or between two species carried by two fluids to occur), or the like.

Non-limiting examples of systems for manipulating fluids, droplets, and/or other species are discussed below. Additional examples of suitable manipulation systems can also be seen in U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; U.S. patent application Ser. No. 11/024,228, filed Dec. 28, 2004, entitled "Method and Apparatus for Fluid Dispersion," by Stone, et al., now U.S. Pat. No. 7,708,949, issued May 4, 2010; U.S. patent application Ser. No. 11/885,306, filed Aug. 29, 2007, entitled "Method and Apparatus for Forming Multiple Emulsions," by Weitz, et al., published as U.S. Patent Application Publication No. 2009/0131543 on May 21, 2009; and U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007; each of which is incorporated herein by reference in its entirety.

Fluids may be delivered into channels within a device via one or more fluid sources. Any suitable source of fluid can be used, and in some cases, more than one source of fluid is used. For example, a pump, gravity, capillary action, surface tension, electroosmosis, centrifugal forces, etc. may be used to deliver a fluid from a fluid source into one or more channels in the device. A vacuum (e.g., from a vacuum pump or other suitable vacuum source) can also be used in some embodiments. Non-limiting examples of pumps include syringe pumps, peristaltic pumps, pressurized fluid sources, or the like. The device can have any number of fluid sources associated with it, for example, 1, 2, 3, 4, 5, 6, 7, 8, 9, 10, etc., or more fluid sources. The fluid sources need not be used to deliver fluid into the same channel, e.g., a first fluid source can deliver a first fluid to a first channel while a second fluid source can deliver a second fluid to a second channel, etc. In some cases, two or more channels are arranged to intersect at one or more intersections. There may be any number of fluidic channel intersections within the device, for example, 2, 3, 4, 5, 6, etc., or more intersections.

A variety of materials and methods, according to certain aspects of the invention, can be used to form devices or components such as those described herein, e.g., channels such as microfluidic channels, chambers, etc. For example, various devices or components can be formed from solid materials, in which the channels can be formed via micromachining, film deposition processes such as spin coating and chemical vapor deposition, physical vapor deposition, laser fabrication, photolithographic techniques, etching methods including wet chemical or plasma processes, electrodeposition, and the like. See, for example, *Scientific American,* 248:44-55, 1983 (Angell, et al).

In one set of embodiments, various structures or components of the devices described herein can be formed of a polymer, for example, an elastomeric polymer such as polydimethylsiloxane ("PDMS"), polytetrafluoroethylene ("PTFE" or Teflon®), or the like. For instance, according to one embodiment, a channel such as a microfluidic channel may be implemented by fabricating the fluidic system separately using PDMS or other soft lithography techniques (details of soft lithography techniques suitable for this embodiment are discussed in the references entitled "Soft Lithography," by Younan Xia and George M. Whitesides, published in the *Annual Review of Material Science,* 1998, Vol. 28, pages 153-184, and "Soft Lithography in Biology and Biochemistry," by George M. Whitesides, Emanuele Ostuni, Shuichi Takayama, Xingyu Jiang and Donald E. Ingber, published in the *Annual Review of Biomedical Engineering,* 2001, Vol. 3, pages 335-373; each of these references is incorporated herein by reference).

Other examples of potentially suitable polymers include, but are not limited to, polyethylene terephthalate (PET), polyacrylate, polymethacrylate, polycarbonate, polystyrene, polyethylene, polypropylene, polyvinylchloride, cyclic olefin copolymer (COC), polytetrafluoroethylene, a fluorinated polymer, a silicone such as polydimethylsiloxane, polyvinylidene chloride, bis-benzocyclobutene ("BCB"), a polyimide, a fluorinated derivative of a polyimide, or the like. Combinations, copolymers, or blends involving polymers including those described above are also envisioned. The device may also be formed from composite materials, for example, a composite of a polymer and a semiconductor material.

In some embodiments, various structures or components of the device are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, waxes, metals, or mixtures or composites thereof heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are used in certain embodiments, for example, the silicone elastomer polydimethylsiloxane. Non-limiting examples of PDMS polymers include those sold under the trademark Sylgard by Dow Chemical Co., Midland, MI, and particularly Sylgard 182, Sylgard 184, and Sylgard 186. Silicone polymers including PDMS have several beneficial properties simplifying fabrication of various structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, at least about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures or channels from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, structures can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.,* 70:474-480, 1998 (Duffy et al.), incorporated herein by reference.

Another advantage to forming channels or other structures (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In some aspects, such devices may be produced using more than one layer or substrate, e.g., more than one layer of PDMS. For instance, devices having channels with multiple heights and/or devices having interfaces positioned such as described herein may be produced using more than one layer or substrate, which may then be assembled or bonded together, e.g., e.g., using plasma bonding, to produce the final device. As a specific example, a device as discussed herein may be molded from masters comprising two or more layers of photoresists, e.g., where two PDMS molds are then bonded together by activating the PDMS surfaces using $O_2$ plasma or other suitable techniques. For example, in some cases, the masters from which the PDMS device is cast may contain one or multiple layers of photoresist, e.g., to form a 3D device. In some embodiments, one or more of the layers may have one or more mating protrusions and/or indentations which are aligned to properly align the layers, e.g., in a lock-and-key fashion. For example, a first layer may have a protrusion (having any suitable shape) and a second layer may have a corresponding indentation which can receive the protrusion, thereby causing the two layers to become properly aligned with respect to each other.

In some aspects, one or more walls or portions of a channel may be coated, e.g., with a coating material, including photoactive coating materials. For example, in some embodiments, each of the microfluidic channels at the common junction may have substantially the same hydrophobicity, although in other embodiments, various channels may have different hydrophobicities. For example a first channel (or set of channels) at a common junction may exhibit a first hydrophobicity, while the other channels may exhibit a second hydrophobicity different from the first hydrophobicity, e.g., exhibiting a hydrophobicity that is greater or less than the first hydrophobicity. Non-limiting examples of systems and methods for coating microfluidic channels, for example, with sol-gel coatings, may be seen in International Patent Application No. PCT/US2009/000850, filed Feb. 11, 2009, entitled "Surfaces, Including Microfluidic Channels, With Controlled Wetting Properties," by Abate, et al., published as WO 2009/120254 on Oct. 1, 2009, and International Patent Application No. PCT/US2008/009477, filed Aug. 7, 2008, entitled "Metal Oxide Coating on Surfaces," by Weitz, et al., published as WO 2009/020633 on Feb. 12, 2009, each incorporated herein by reference in its entirety. Other examples of coatings include polymers, metals, or ceramic coatings, e.g., using techniques known to those of ordinary skill in the art.

As mentioned, in some cases, some or all of the channels may be coated, or otherwise treated such that some or all of the channels, including the inlet and daughter channels, each have substantially the same hydrophilicity. The coating materials can be used in certain instances to control and/or alter the hydrophobicity of the wall of a channel. In some embodiments, a sol-gel is provided that can be formed as a coating on a substrate such as the wall of a channel such as a microfluidic channel. One or more portions of the sol-gel can be reacted to alter its hydrophobicity, in some cases. For example, a portion of the sol-gel may be exposed to light, such as ultraviolet light, which can be used to induce a chemical reaction in the sol-gel that alters its hydrophobicity. The sol-gel may include a photoinitiator which, upon exposure to light, produces radicals. Optionally, the photoinitiator is conjugated to a silane or other material within the sol-gel. The radicals so produced may be used to cause a condensation or polymerization reaction to occur on the surface of the sol-gel, thus altering the hydrophobicity of the surface. In some cases, various portions may be reacted or left unreacted, e.g., by controlling exposure to light (for instance, using a mask).

A variety of definitions are now provided which will aid in understanding various aspects of the invention. Following, and interspersed with these definitions, is further disclosure that will more fully describe the invention.

A "droplet," as used herein, is an isolated portion of a first fluid that is completely surrounded by a second fluid. In some cases, the first fluid and the second fluid are substantially immiscible. It is to be noted that a droplet is not necessarily spherical, but may assume other shapes as well, for example, depending on the external environment. The diameter of a droplet, in a non-spherical droplet, is the diameter of a perfect mathematical sphere having the same volume as the non-spherical droplet. The droplets may be created using any suitable technique, as previously discussed.

As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. If two or more fluids are present, each fluid may be independently selected among essentially any fluids (liquids, gases, and the like) by those of ordinary skill in the art.

Certain embodiments of the present invention provide a plurality of droplets. In some embodiments, the plurality of droplets is formed from a first fluid, and may be substantially surrounded by a second fluid. As used herein, a droplet is "surrounded" by a fluid if a closed loop can be drawn around the droplet through only the fluid. A droplet is "completely surrounded" if closed loops going through only the fluid can be drawn around the droplet regardless of direction. A droplet is "substantially surrounded" if the loops going through only the fluid can be drawn around the droplet depending on the direction (e.g., in some cases, a loop around the droplet will comprise mostly of the fluid by may also comprise a second fluid, or a second droplet, etc.).

In most, but not all embodiments, the droplets and the fluid containing the droplets are substantially immiscible. In some cases, however, they may be miscible. In some cases, a hydrophilic liquid may be suspended in a hydrophobic liquid, a hydrophobic liquid may be suspended in a hydrophilic liquid, a gas bubble may be suspended in a liquid, etc. Typically, a hydrophobic liquid and a hydrophilic liquid are substantially immiscible with respect to each other, where the hydrophilic liquid has a greater affinity to water than does the hydrophobic liquid. Examples of hydrophilic liquids include, but are not limited to, water and other aqueous solutions comprising water, such as cell or biological media, ethanol, salt solutions, etc. Examples of hydrophobic liquids include, but are not limited to, oils such as hydrocarbons, silicon oils, fluorocarbon oils, organic solvents etc. In some cases, two fluids can be selected to be substantially immiscible within the time frame of formation of a stream of fluids. Those of ordinary skill in the art can select suitable substantially miscible or substantially immiscible fluids, using contact angle measurements or the like, to carry out the techniques of the invention.

The following documents are incorporated herein by reference in their entireties: International Patent Application No. PCT/US2015/026443, filed Apr. 17, 2015, entitled "Systems and Methods for Barcoding Nucleic Acids," by Weitz, et al, published as WO 2015/164212 on Oct. 29, 2015; International Patent Application No. PCT/US2014/052271, filed Aug. 22, 2014, entitled "Determination of Immune Cells And Other Cells," by Heyman, et al., published as WO 2015/031190 on Mar. 5, 2015; International Patent Application No. PCT/US04/10903, filed Apr. 9, 2004, entitled "Formation and Control of Fluidic Species," by Link, et al., published as WO 2004/091763 on Oct. 28, 2004; International Patent Application No. PCT/US03/20542, filed Jun. 30, 2003, entitled "Method and Apparatus for Fluid Dispersion," by Stone, et al., published as WO 2004/002627 on Jan. 8, 2004; International Patent Application No. PCT/US04/27912, filed Aug. 27, 2004, entitled "Electronic Control of Fluidic Species," by Link, et al., published as WO 2005/021151 on Mar. 10, 2005; and U.S. Pat. No. 8,337,778. Also incorporated herein by reference in their entireties are International Patent Application No. PCT/US2008/008563, filed Jul. 11, 2008, entitled "Droplet-Based Selection," by Weitz, et al., published as WO 2009/011808 on Jan. 22, 2009; and International Patent Application No. PCT/US2009/004037, filed Jul. 10, 2009, entitled "Systems and Methods of Droplet-Based Selection," by Weitz, et al., published as WO 2010/005593 on Jul. 10, 2009. In addition, U.S. Provisional Patent Application Ser. No. 62/313,339, filed Mar. 25, 2016, entitled "Microfluidic Determination of Immune Cells," by Weitz, et al. is incorporated herein by reference in its entirety.

The following examples are intended to illustrate certain embodiments of the present invention, but do not exemplify the full scope of the invention.

Example 1

This example illustrates bead-based fluorescence concentration assays in microfluidic droplets. Components of the bead assay are microbeads coated with a capture antibody, and fluorescently labeled detection antibodies. Both antibodies are directed against the same target protein, for example the cytokine interferon gamma (IFN-γ). Microfluidics is used to create droplets containing the capture bead, the detection antibody, cell growth medium, and effector and target cells. If the cells interact actively with each other, one or both of the cells may secrete cytokines of interest within a few hours of incubation. The cytokines can attach to the capture and detection antibodies, resulting in concentration of the fluorescent detection antibody onto the bead. The bead may fluoresce brightly upon laser excitation, and the freely dispersed fluorescent signal within the droplet may be reduced (see FIGS. 1 and 2). If the encapsulated cells do not interact, the cytokine of interest is not secreted and the bead remains non-fluorescent. Thus presence of a bright bead indicates presence of the cytokine of interest.

FIG. 1 shows a bead assay for cytokine detection, as one non-limiting example. Streptavidin coated polystyrene beads are coated with biotinylated capture antibody (produced in an animal with the target cytokine as the antigen), making a capture bead. A detection antibody is stained with a fluorophore (e.g., produced in an animal with the target cytokine as the antigen). The cytokine attaches to the capture bead and the detection antibody upon contact. The cytokine is thus captured onto the bead with the fluorescent detection antibody sticking out on the surface, making the bead appear fluorescent.

Figure 2:
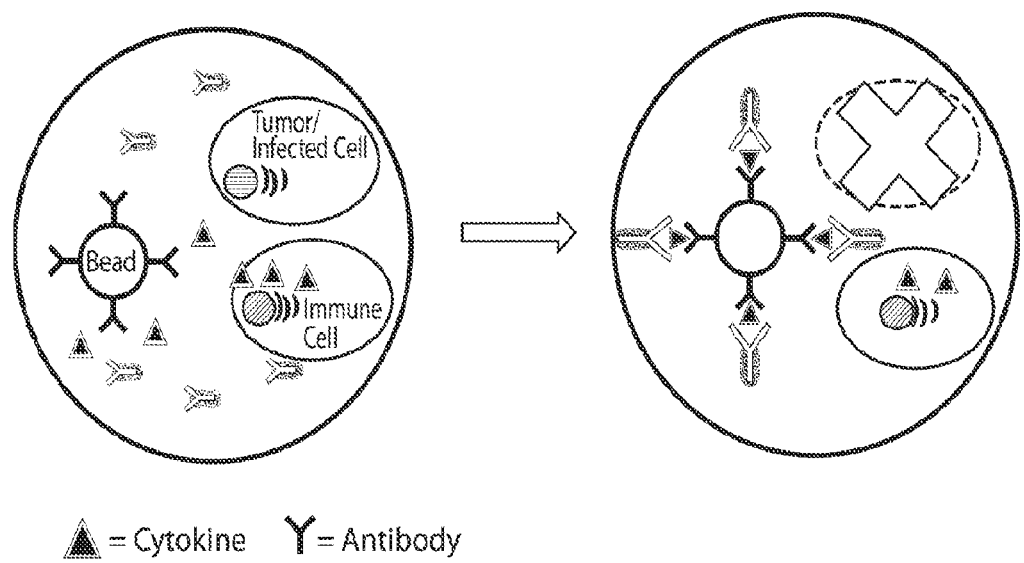
FIG. 2 illustrates a cell identification technique according to another embodiment of the invention.

FIG. 2 shows effector cell identification with the bead assay in droplets. The capture bead, the fluorescent detection antibody, and the two types of cells (immune cell and tumor/infected cell) are co-encapsulated in one droplet. Upon cell-cell contact, if the receptors of the immune cell match some antigens presented by the diseased cell, the immune cell will be activated to secrets cytokine and kill the diseased cell, making the immune cell an effector cell.

In some cases, a bead can be coated with several different capture antibodies and the corresponding detection antibody species, each labeled with a different fluorescent molecule, can be included in the droplets. In this way, multiple cytokines can be detected simultaneously.

Example 2

This example illustrates a killing assay in droplets. In the killing assay, a dye that detects cell death can be incorporated into the droplets together with the interacting cells. Within the same few hours when cytokines are secreted, some of the target cells may be killed, which can be stained by a cell death dye. Fluorescence detection methods (fluorescence microscopy, photomultiplier tubes, etc.) can pick up this dye signal and display the dying/dead cell in a different color from that used in the fluorescence concentration read-out. The combination of an immune cell cytokine-secretion-signal and a target cell-death-signal reduces false-positives and leads to more accurate identification and sorting of effector cells.

Example 3

Figure 5:
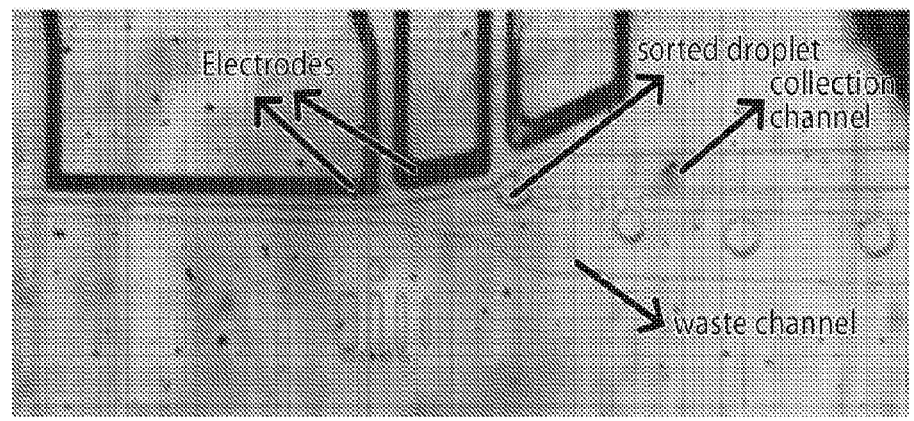
FIG. 5 illustrates droplet sorting in yet another embodiment of the invention.

This example illustrates effector cell identification and selection. Effector cell selection is performed by an opto-electrical sorting method. The droplets flow through a microfluidic device channel and pass through a laser excitation and fluorescence detection zone located upstream of waste and sort channels. When the droplets cross the laser spot, the optical signals from the fluorescent excitation are sent to Photomultiplier Tubes (PMTs). When the PMT detects an optical signal from the droplet that is above a user-defined threshold, the electrodes are activated to generate an electrical field. A droplet flowing through this field experiences a dielectric force that directs it into the collection channel. When the electrodes are not activated, droplets flow into the waste channel. In the effector cell selection method, the electrodes are activated when one PMT detects a bright bead (via the fluorescent detection antibody) while a second PMT detects the dead cell (via the dye). The sorting process is shown in FIG. 5. After droplets have been analyzed, sorted droplets can be broken, e.g., with PFO (per-fluoro octanol) to release the effector cells for further study (e.g., DNA sequencing, T cell receptor identification, or analysis of mRNA levels) or to expand cell number in vitro.

Figure 3:
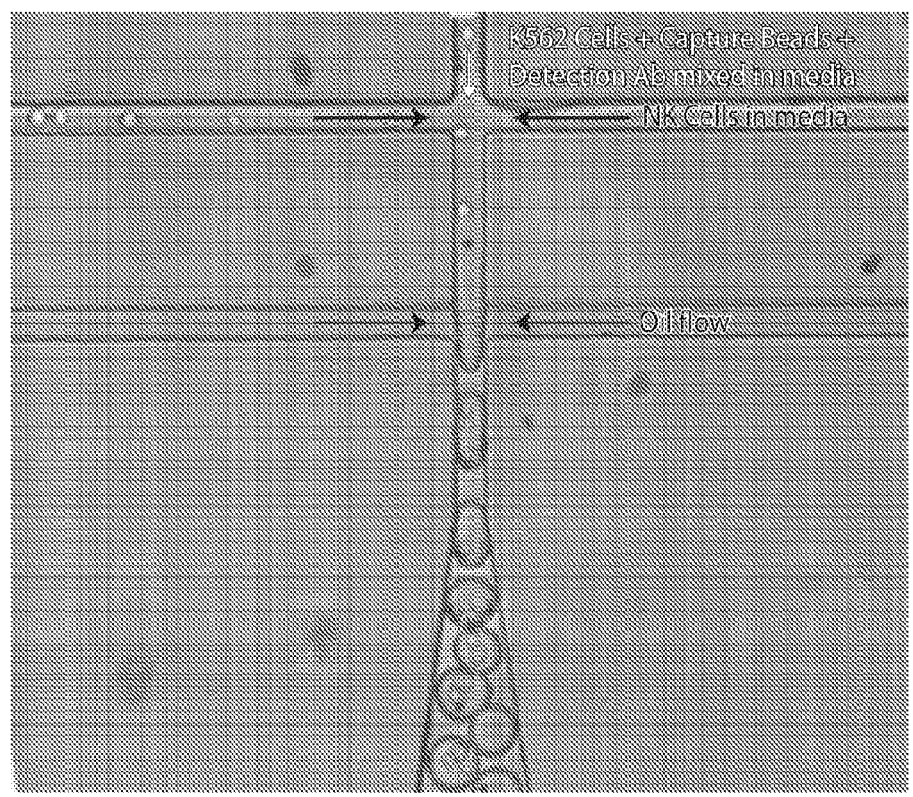
FIG. 3 illustrates encapsulation of cells in droplets, in one embodiment of the invention.

FIG. 3 illustrates encapsulation of the bead assay and two type of cells into droplets, with Natural Killing cell (a type of immune cell) and K562 cell (a tumor cell line) as an example. The two types of cells come from two different inlets with one inlet hosting the bead, detection antibody and the diseased cells. Carrier oil comes from the side to cut the water-based phase into droplets after the previous two inlets of reagents in media are mixed into one stream.

Figure 4A:
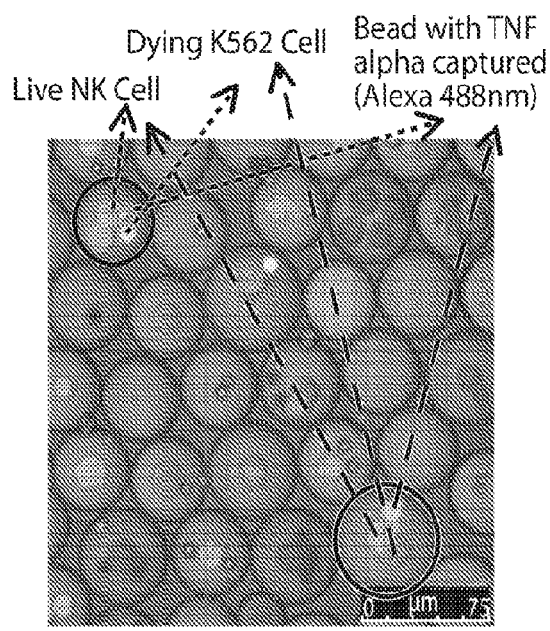
FIGS. 4A-4B illustrate an assay in accordance with another embodiment of the invention.
Figure 4B:
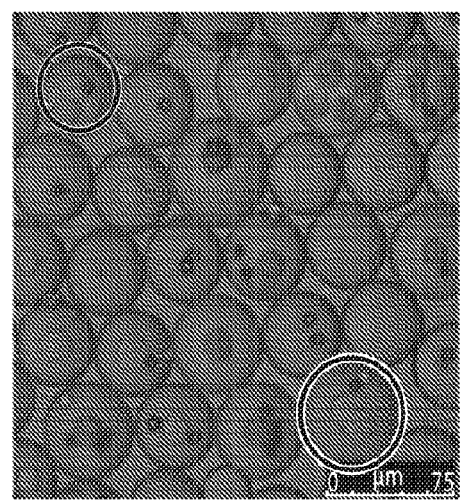

FIG. 4 shows detection of a killing event by detecting TNF-alpha (TNF-α) secretion after 4 hours of cell incubation at 37° C. under a confocal microscope: A fluorescent image (FIG. 4A) with a white light image (FIG. 4B). The background has some fluorescence due to the fact that the detection antibody (anti-TNF-alpha) is free-floating in the droplet. NK cells will appear red as they were stained with a red dye and killed K562 cells have orange nuclei as an orange dye that is incorporated stains the nuclei acid. The bead will appear green when two cells are present due to the secretion of TNF-alpha by the NK cell, the capture of the secreted TNF-alpha and the aggregation of the detection antibody onto the bead. If the two different cell types are together, then a green bead can be observed, indicating secretion of cytokine.

FIG. 5 shows droplet sorting for effector cell selection. The dark black lines are the electrodes which send in the high voltage needed to apply a force to the droplets by electrophoresis. The lighter lines are the microfluidic sorting channels. The feature underneath the sorting channel is a set of size markers ranging from 5 micrometers to 30 micrometers. The image shows one selected droplet with a bright bead being pushed upwards into the collection channel.

Figure 6A:
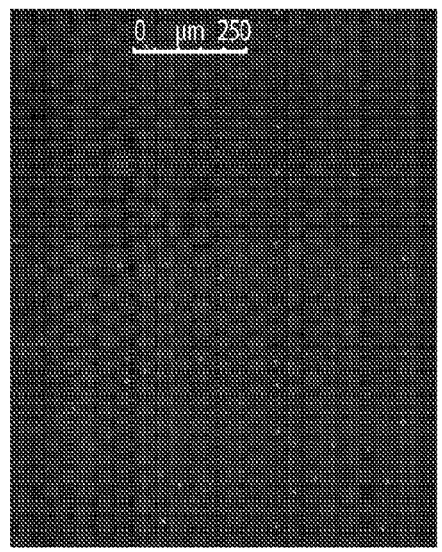
FIGS. 6A-6B illustrate enrichment of effector cells, in still another embodiment of the invention.
Figure 6B:
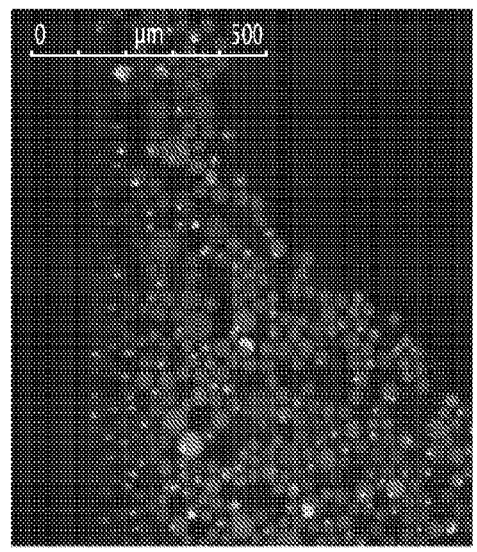

FIG. 6 shows effector cell enrichment before (FIG. 6A) and after (FIG. 6B) sorting. Bright beads represents cytokines captured, meaning the presence of an effector cell and a diseased cell. Thus droplets with effector cells are identified by bright beads.

Example 4

This example illustrates nucleic acid analysis. Nucleic acid analysis can be performed on droplet encapsulated cells in several ways.

For example, sorted droplets can be dispensed into multiwell plates at less than one drop per well. Drops are then broken and reagents for nucleic acid analysis are added. Effector and target cells remain associated as they were in the droplets.

Bead-based, in-droplet barcoding can be implemented by including a barcoding polystyrene bead or spherical hydrogel during drop formation. See, e.g., U.S. Pat. Apl. Pub. No. 2015-0298091, incorporated herein by reference in its entirety. This allows next-generation sequencing of many cells while maintaining the association between cells that were encapsulated in the same drop. To avoid interfering with the effector-target functional assay, reagents for nucleic acid sequencing must be added (e.g., by microfluidic picoinjection) after the killing assay is performed. See, for example, U.S. Pat. Apl. Pub. No. 2012-0132288, incorporated herein by reference in its entirety.

Example 5

This example illustrates identification of the peptide targets recognized by T cells with desired specificity/killing activity. One use of this platform may be to identify the peptide targets of useful T cells. Each cytotoxic CD8+ T cell presents may copies of one species of T cell receptor (TCR) on its surface. The TCR of a useful T cell may recognize a peptide presented in the MHC class one molecule on the surface of infected cells or cancer cells. In some cases, this peptide may not be presented on the surface of normal (non-infected, non-cancerous, etc.) cells and the "useful" T cells may have no interaction with normal cells.

It can be difficult to identify peptides that are uniquely, or primarily, seen on the surface of cancer cells. However, droplets maintain the pairing of T cell and target cell, and thus can link T cell information to target cell information. For example, after a droplet in which a T cell kills a cancer cell is sorted the nucleic acids of both cells can be sequenced and analyzed as a pair.

This ability to maintain a relationship between a killing T-cell's TCR and the target cell can be used with high-throughput sequencing and molecular biology. In one application, exome sequencing is performed on autologous tumor and non-tumor cells, and mutant proteins unique to the cancer cell are identified. Expression vectors can be created encoding the mutant proteins, autologous cells can be transfected, and the transfected cells used with T cells of interest in in-droplet immune activation/killing assays. The drops containing killing events can be sorted and then the paired TCRs and transfected DNA can be sequenced. This may identify the mutant protein recognized by the TCR. The mutant peptide displayed in the target cell class I MHC can then by identified by repeating the process using vectors expressing fragments of the mutant protein.

This ability to identify immune-critical peptides can be useful in identifying "public" epitopes, i.e., those that are found in the tumors of many different subjects, and thus may identify generally useful TCRs, e.g., which can be used to treat numerous subjects. In addition, in some cases, the peptides may be used to create vaccines for subjects having cancers that present those particular peptides. In some cases, an ability to identify cancer-specific peptides may be useful in categorizing cancers so that appropriate treatments are used.

Example 6

This example illustrates various materials and methods for use in certain embodiments of the invention.

Beads, antibodies, biotin, and dyes. Streptavidin coated polystyrene particles of 6.7 micrometers in size (Cat: SVP-60-5) were obtained from Spherotech Inc. (Lake Forest, IL).

Capture antibodies mouse anti-human TNF-alpha (Cat: MAB610) and mouse anti-human interferon gamma (Cat: MAB2852), and detection antibodies goat anti-human TNF-alpha (Cat: AF-210-NA) and Goat Anti-human interferon gamma (Cat: AF-285-NA) were also obtained from R&D Systems (Lake Forest, IL).

Biotin and all dyes were obtained from ThermoFisher Scientific (Waltham, MA). Biotinylation was done with biotin EZ-Link Sulfo-NHS-SS-Biotin (Cat: 21328) and the respective biotinylation kit (Cat: 21445). Fluorescent staining for the detection antibodies were done with the kit Molecular Probes® Alexa Fluor® 488 (Cat: A20181). The dye used for NK cell staining is CellTracker™ Deep Red (Cat: C34565). The dye for dead K562 cells staining was SYTOX® Orange (Cat: S11368).

Cell lines and cell culturing. Immune cells and tumor cells were obtained from ATCC (Manassas, VA). The immune cells Natural Killer Cells NK92MI (Cat: CRL2408™) is a cell line that is genetically modified to synthesize human Interleukin-2. The tumor cells K-562 (Cat: CCL243™) were derived from a chronic myelogenous leukemia patient.

Most of the ingredients in the Cell Culturing Media were from ThermoFisher Scientific, including alpha-MEM (Cat: A1049001), fetal bovine serum (Cat: 16141079), and horse serum (Cat: 26050088). DMEM (Cat: 10-013-CV) was bought from Corning Inc. (Corning, NY). Folic acid (CAS: 59-30-3), inositol (CAS: 87-89-8) and beta-mercaptoethanol (CAS: 60-24-2) were from Sigma-Aldrich (Natick, MA).

Dropmaking reagents. For the carrier oil, HFE-7500 (Cat: Novec 7500, 3M, Minn.) with 1% w/w of a block copolymer surfactant of perfluorinated polyethers (PFPE) and polyethylene glycol (PEG) (008-FluoroSurfactant, Ran Biotechnologies, MA) was used. The cell-carrying phase was the immune cell culture media. To separate the emulsion, a commercially available demulsifier 1H, 1H, 2H, 2H-perfluoro-1-octanol (CAS: 647-42-7, Sigma-Aldrich) was used. The density matching agent used was Percoll™ (Cat: P1644, Sigma-Aldrich).

Cell culturing. NK cells were maintained at around 300,000 cells/mL in a medium containing alpha-MEM, 12.5% fetal bovine serum, 12.5% horse serum, 0.02 mM folic acid, 0.2 mM inositol, and 0.1 mM beta-mercaptoethanol. K562 Cells were maintained at around 400,000/mL in a medium containing DMEM and 10% fetal bovine serum. The cells were split every two days to avoid crowding and to maintain cell health. Different cell types shall be cultured according to their own guidelines.

Fabrication of microfluidic devices. Polydimethylsiloxane (PDMS) devices were fabricated by curing PDMS on a chip made with photolithography. The PDMS chip was then bonded to a glass slide after surface activation with plasma following standard plasma treatment procedures. The devices were coated with fluorophilic Aquapel (Pittsburgh Glass Works LLC, Pittsburgh, PA) to prevent wetting of drops on the channel walls. Electrodes on the sorter are fabricated on chip using low melting temperature solder.

Assays for cytokine detection and cytolysis. Capture mouse antibodies were biotinylated with Biotin with a biotinylation kit. To prepare the capture beads, first streptavidin coated beads were washed twice with PBS, each by centrifuging at a force equivalent to 10,000× gravity for 60 seconds and removing the supernatant, then the washed streptavidin beads were mixed with biotinylated mouse antibodies in PBS at a relative concentration of $4 \times 10^6$ molecules/bead. The mixture was put on a rotation stage for an hour to allow binding before the stock of capture beads was ready to be used. Detection antibody was stained with the Alexa fluorophore according to the instructions that came with the kit.

Cultured immune cells and tumor cells were prepared according to standard medical guidelines.

On the day of procedure, the two types of cells were counted with a hemocytometer to determine the concentration at which they have grown. Then the required number of cells were taken out in a sterile hood. Immune cells were subsequently stained with CellTracker™ Deep Red by following the instructions that came with the kit.

Then the immune cells were washed to remove the dyes by pelleting them at 200× gravity for 3.5 minutes, removing the immune cell culture media, followed by re-suspending the cells in fresh culture media. Lastly, the immune cells and tumor cells were pelleted separately, most of the media was removed to increase the cell concentration, and the cells were stored into separate Eppendorf tubes on ice.

After cell preparation, the required amount of capture beads were taken out from the stock and washed three times before being mixed with detection antibody and tumor cells in one Eppendorf tube. Immune cell culture Media was then added to make a final concentration of 400,000 cells/mL, 400,000 beads/mL and $1 \times 10^{11}$ detection antibody molecules/mL (or about 250,000 molecules/bead). Immune Cells and the dye Sytox Orange were added to another Eppendorf tube with additional culture media to make a final concentration of 400,000 cells/mL with Sytox Orange at 1 micromolar.

Droplet making. A vacuum supply at around −12 psi (gauge, 1 psi~6894 Pa) was used to drive the microfluidic flow and a fast camera (HiSpec1, Fastec Imaging, USA) was used to image encapsulation. Two different Eppendorf tubes of reagents were loaded into two separate inlets of one device while the carrier oil was loaded into the outer inlet. A syringe vacuum collector was connected to the outlet to collect drops. Droplets making starts once the vacuum is turned on.

Imaging and analysis. Images were taken with a Leica confocal microscope. Analysis was done with Matlab.

Droplet sorting. Droplet sorting was performed with a laser system. See, e.g., U.S. Pat. Apl. Pub. No. 2009/0068170, incorporated herein by reference in its entirety.

Example 7

Figure 7A:
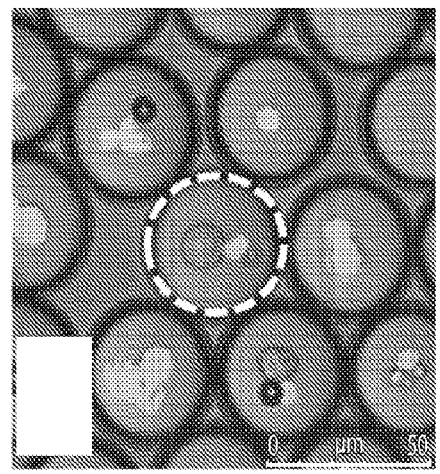
FIGS. 7A-7B illustrate determination of target cells, in one embodiment of the invention.
Figure 7B:
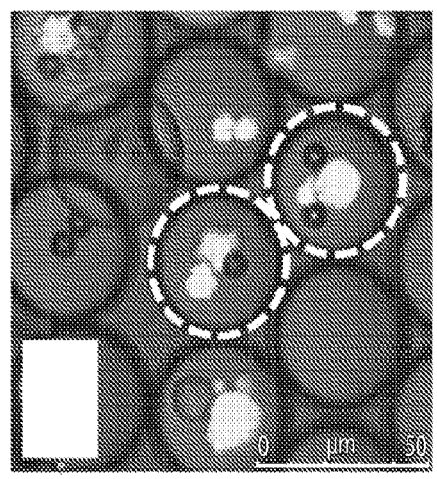

FIGS. 7A-7B illustrates T cells from an OT-1 mouse secrete IFN-gamma when co-encapsulated with peptide-pulsed EL4 target cells. In these figures, OT-1 cells were stained with CellTrace yellow, OVA-pulsed cells EL4 were not stained, while non-pulsed cells were stained with Calcein-AM and fluoresced green. Secreted interferon gamma was captured by monoclonal anti-interferon gamma on particles and was detected with biotinylated goat anti-mouse+alexa-647 streptavidin. Droplets were incubated 3 hours at 37° C. and were imaged. In FIG. 7A, the droplet circled with a dotted line contained an OT-1 cell and at pulsed target cell and the co-encapsulated bead was bright, indicating secretion of INF-gamma. In FIG. 7B, the circled droplets contained an OT-1 cell and a non-pulsed target cell, indicating that the OT-1 cells were not activated in response to an interaction with non-pulsed target cells.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
    flowing immune cells in a first stream within a first microchannel of a microfluidic device, target cells in a second stream within a second microchannel of the microfluidic device, a particle attached to a first antibody with binding specificity for a target cytokine, a second antibody with binding specificity for the target cytokine, and a first label that determines cell viability of the target cell, wherein the particle attached to the first antibody is flowed in either the first stream or the second stream, wherein the second antibody is flowed in either the first stream or the second stream, and wherein the first label is flowed in either the first stream or the second stream;
    co-encapsulating, in a droplet in the microfluidic device, only one flowing immune cell from the first stream, only one flowing target cell from the second stream, the flowing particle attached to the first antibody with binding specificity for the target cytokine, the flowing second antibody with binding specificity for the target cytokine, and the flowing first label that determines cell viability of the target cell, wherein the second antibody comprises a second label that is different from the first label, and wherein release of the target cytokine is indicative of activation of the immune cell resulting from an interaction between the target cell and the immune cell, wherein neither the only one immune cell nor the only one target cell are individually encapsulated in a prior droplet before co-encapsulation in the droplet in the microfluidic device;
    determining presence or absence of the first label that determines cell viability of the target cell;
    determining presence or absence of the target cytokine within the droplet in the microfluidic device by determining presence or absence of the second label concentrated around the particle within the droplet, wherein determination of the presence of the target cytokine occurs after the target cytokine binds to the first antibody and the second antibody; and
    sorting the droplet based on the detected presence or absence of the first label and detected presence or absence of the second label, thereby obtaining a population of droplets having a presence of the first label and presence of the second label.

2. The method of claim 1, wherein the first label comprises a first fluorescent entity.

3. The method of claim 1, wherein the first label comprises one or more of calcein, a calcein derivative, Alexa Fluor 488, or a fluorescent green dye.

4. The method of claim 1, wherein the second antibody comprises an anti-interferon-gamma (anti-IFN-gamma) antibody.

5. The method of claim 1, wherein the particle comprises polystyrene.

6. The method of claim 1, wherein the particle comprises a streptavidin coating, and the first antibody comprises a biotinylated portion.

7. The method of claim 1, wherein the target cytokine includes TNF-alpha.

8. The method of claim 1, wherein the target cytokine includes IFN-gamma.

9. The method of claim 1, wherein the immune cell is a T-cell.

10. The method of claim 1, wherein the immune cell is a CD8+ T-cell.

11. The method of claim 1, wherein the immune cell is a B-cell.

12. The method of claim 1, wherein the target cell is a cancer cell.

13. The method of claim 1, wherein the target cell is a virally-infected cell.

14. The method of claim 1, comprising simultaneously containing the only one immune cell, the only one target cell, the particle attached to the first antibody, and the second antibody in the microfluidic droplet.

15. The method of claim 1, wherein detection of presence of the target cytokine comprises detecting distribution of a label of the second antibody around the particle attached to the first antibody.

16. The method of claim 1, wherein determination of the presence or absence of the target cytokine within the droplet does not include a wash step.

17. The method of claim 1, wherein co-encapsulating, in the droplet in the microfluidic device, comprises:
co-encapsulating the only one immune cell and the only one target cell at a junction downstream from where the first microchannel and the second microchannel meet.

18. The method of claim 1, further comprising:
collecting the immune cell from the sorted droplet; and
sequencing at least a receptor of the immune cell.

19. The method of claim 1, wherein the step of co-encapsulating further comprises co-encapsulating one or more additional labels in the droplet that are different from the first label and the second label.

20. The method of claim 19, further comprising detecting presence or absence of each of the one or more additional labels, wherein the sorting of the droplet is further based on the detected presence or absence of each of the one or more additional labels, and wherein the population of droplets further have a presence of each of the one or more additional labels.

* * * * *